United States Patent
Sicheri et al.

(10) Patent No.: US 12,186,401 B2
(45) Date of Patent: Jan. 7, 2025

(54) AMIDE-BASED PROTEOLYSIS MODULATORS OF B-RAPIDLY ACCELERATED FIBROSARCOMA (BRAF) AND ASSOCIATED USES

(71) Applicants: Ontario Institute for Cancer Research (OICR), Toronto (CA); Sinai Health System, Toronto (CA)

(72) Inventors: Frank Sicheri, Toronto (CA); Ganna Posternak, Toronto (CA); Gennady Poda, Toronto (CA)

(73) Assignee: Ontario Institute for Cancer Research (OICR) and Sinai Health System, Toronto (CA)

( * ) Notice: Subject to any disclaimer, the term of this patent is extended or adjusted under 35 U.S.C. 154(b) by 703 days.

(21) Appl. No.: 17/310,837

(22) PCT Filed: Mar. 2, 2020

(86) PCT No.: PCT/CA2020/050280
§ 371 (c)(1),
(2) Date: Aug. 26, 2021

(87) PCT Pub. No.: WO2020/176983
PCT Pub. Date: Sep. 10, 2020

(65) Prior Publication Data
US 2022/0125936 A1    Apr. 28, 2022

Related U.S. Application Data

(60) Provisional application No. 62/812,567, filed on Mar. 1, 2019.

(51) Int. Cl.
| | |
|---|---|
| A61K 47/55 | (2017.01) |
| A61K 47/54 | (2017.01) |
| A61P 35/00 | (2006.01) |
| C07D 471/04 | (2006.01) |

(52) U.S. Cl.
CPC .............. *A61K 47/55* (2017.08); *A61K 47/54* (2017.08); *A61K 47/545* (2017.08); *A61P 35/00* (2018.01)

(58) Field of Classification Search
CPC ....... A61P 35/00; C07D 471/04; A61K 47/55; A61K 47/54
See application file for complete search history.

(56) References Cited

U.S. PATENT DOCUMENTS

| 9,938,264 B2 | 4/2018 | Crews et al. |
|---|---|---|
| 2018/0179183 A1 | 6/2018 | Crew et al. |
| 2018/0228907 A1 | 8/2018 | Crew et al. |

FOREIGN PATENT DOCUMENTS

| CA | 3047784 A1 | 6/2018 |
|---|---|---|
| WO | 2008119741 A2 | 10/2008 |
| WO | 2015160845 A2 | 10/2015 |
| WO | 2016197032 A1 | 12/2016 |
| WO | 2017079267 A1 | 5/2017 |
| WO | 2018119448 A1 | 6/2018 |
| WO | 2019199816 A1 | 10/2019 |

OTHER PUBLICATIONS

Posternak et al., Nature Chemical Biology, 2020, 16(11), 1170.*
Han et al., J. Med. Chem. 2020, 63(8), 4069-4080.*
International Search Report and Written Opinion of corresponding PCT/CA2020/050280 dated May 28, 2020.
Aginian, Bogos et al., "Current Insights of BRAF Inhibitors in Cancer", J. Med. Chem., 2018, 61, pp. 5575-5793.
Grasso, Michael Joseph, "Development and Characterization of Novel Raf Dimer Inhibitors to Target Brafv600e Inhibitor Resistance", 2018, Publicly Accessible Penn Dissertations, pp. 1-166.
Jarvis, Lisa M. "Pfizer Inks Protein Degradation Deal with Arvinas", News of the Week, vol. 96, Issue 2, p. 8.
Chen, Hong; et al. "Pomalidomide hybrids act as proteolysis targeting chimeras: Synthesis, anticancer activity and B-Raf degradation" Bioorganic Chemistry 2019, 87, 191-199.

* cited by examiner

*Primary Examiner* — Sun Jae Yoo
(74) *Attorney, Agent, or Firm* — Smart & Biggar LP; Sandra Marone

(57) ABSTRACT

The present application relates to novel compounds of Formula (I) containing a E3 ubiquitin ligase binding moiety linked to a Raf protein kinase binding moiety. The present application also includes methods and uses of the compounds, for example, for inhibiting and/or degrading V600E mutant B-Raf. I

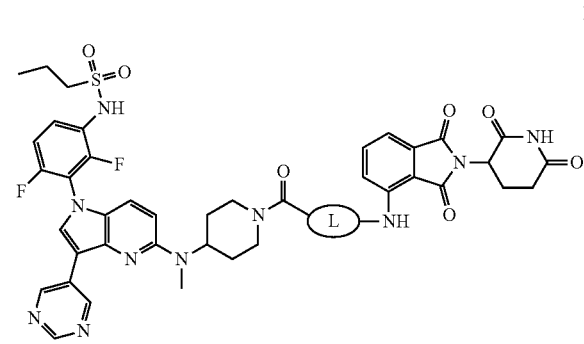

20 Claims, 5 Drawing Sheets

AMIDE-BASED PROTEOLYSIS MODULATORS OF B-RAPIDLY ACCELERATED FIBROSARCOMA (BRAF) AND ASSOCIATED USES

RELATED APPLICATIONS

The present application is a National Phase Entry of co-pending International Application No. PCT/CA2020/050280 filed on Mar. 2, 2020, which claims the benefit of priority of U.S. provisional patent application No. 62/812,567 filed on Mar. 1, 2019, the contents of both of which are incorporated herein by reference in their entirety.

FIELD

The present application relates to chimeric compounds containing a cereblon E3 ubiquitin ligase binding moiety linked to a Raf protein kinase binding moiety, as well as processes for their preparation and methods of using such compounds and compositions.

BACKGROUND

The RAS-RAF-ERK pathway is a biological signaling cascade that transmits extra-cellular signals emanating from growth factor receptor tyrosine kinases through the cellular cytoplasm. A key component of this signaling cascade occurs when activated RAS directs plasma membrane recruitment and activation of catalytically competent A-Raf, B-Raf and c-Raf protein kinases. Through the formation of allosteric homo- and heterodimers involving A-Raf, B-Raf, c-Raf and their catalytically incompetent paralogues KSR1 and KSR2, the catalytically active Raf kinases phosphorylate MEK1/2 at one of two serine residues. Phosphorylated MEK1/2 in turn signals through ERK kinase by phosphorylating and activating it at two serine residues. Finally, activated ERK signals through various cytosolic and nuclear substrates to induce cellular proliferation and survival mechanisms.

Since the RAS-RAF-ERK pathway is essential to cellular growth and survival, multi-cellular organisms have evolved various mechanisms to insure its proper regulation and balance. Because of these tight requirements for the control of normal growth and homeostasis, it has become evident that aberrant upregulation of the pathway plays a highly prevalent role in human cancers. In fact, it is estimated that approximately one third of human cancers are impacted by mutations in the Ras-Raf-ERK signaling pathway. Although the most common mutation among them is Ras itself, efforts to "drug" this target have proven largely unsuccessful. In contrast, downstream members of the pathway, including Raf, MEK and ERK have proven much more amenable to therapeutic targeting. Among them, mutations of B-Raf are particularly prevalent in various tumor types, and therefore inhibiting this target with small molecule inhibitors is of strong interest. As a result of efforts spanning many years, multiple drugs targeting B-Raf are now either marketed or in advanced clinical trials. Currently, agents that have been approved for the treatment of melanoma driven by the V600E B-Raf mutant include vemurafenib, dabrafenib and encorafenib.

Despite impressive initial clinical responses seen with marketed B-Raf inhibitors, the use of these drugs has important limitations. First, in the large majority of cases initial responses to B-Raf kinase inhibitors gives way to relapse that typically occurs within 6 months (acquired, or secondary resistance). In addition, many mutant B-Raf tumours fail to show an initial response to B-Raf inhibitors (intrinsic resistance).

While the mechanisms of primary and secondary resistance are multifaceted, they commonly involve splice variants and amplifications in Raf that directly impair inhibitor binding or mutations to pathway components upstream of RAF that render inhibitor binding to B-Raf ineffective in restraining Raf signal transmission. Examples of the latter include activating mutations in Ras or in growth factor receptor kinases.

Finally, clinical agents such as vemurafenib and dabrafenib, through binding to the B-Raf active site in non-mutated tissues, are known to promote the formation of wild type B-Raf and c-Raf homo and heterodimers. This results in allosteric activation Raf kinase activity and in turn leads to signaling flux through the ERK cascade. In turn, this increased flux gives rise to wild-type B-Raf mediated hyperproliferation (paradoxical activation), which leads to subcutaneous carcinoma in a subset of patients. Given the limitations of current B-Raf inhibitors, new treatment modalities are under investigation. One such approach is to discover agents which, instead of or in addition to inhibiting the catalytic activity of b-Raf, lead to the degradation of B-Raf protein itself.

One strategy to achieve the degradation of a target protein in the confines of a living cell is to harness the power of the ubiquitin proteolytic system (UPS), a cellular process whereby attachment of the small protein ubiquitin (Ub) to a target protein can render it a substrate for proteolytic destruction by the 26S proteasome. The process of ubiquination is mediated by a cascade of three enzyme classes, denoted E1, E2, and E3. Chief amongst these, the E3 ligases, which number over 600 in humans, confer specificity by directly engaging the target protein to facilitate the final transfer step of the ubiquitination process. Proteolysis targeting chimeras, PROTACs, are a class of bi-functional small molecules engineered to simultaneously engage a cellular E3 and a non-native target protein of interest (see FIG. 1). Simultaneous binding of the PROTAC renders the target protein of interest an efficient artificial substrate for ubiquitination and destruction by the 26S proteasome.

Distinct classes of E3 ligases have been investigated as effectors of degradation of target proteins in the design of bifunctional PROTACS. Two common E3 ligases that have been utilized are von Hippel-Lindau (VHL) protein and cereblon (CRBN). Initial encouraging efforts in the construction of PROTACS incorporated a hydroxylated pentapeptide VHL-recognition motif. Subsequently, the development of more potent and cell-permeable VHL ligands (*J. Med. Chem.* 2014, 57, 8657-8663) has led to a considerable expansion of the PROTAC field. To date, diverse classes of protein targets have been successfully targeted for intracellular degradation by VHL-containing PROTACS, including kinases, bromodomains and estrogen hormone receptors (*Biochemical Journal*, 2017, 474 1127). In 2015, reports from the laboratories of Craig Crews (*Chemistry & Biology*, 2015, 22, 755-763) and James Bradner (*Science*, 2015, 348, 1376) demonstrated that phthalimide-based ligands of the thalidomide class of CRBN-binding drugs could also successfully be employed to produce bifunctional PROTACS. Two of these initial examples were directed towards the targeted degradation of the epigenetic protein BRD4. However, similar to VHL-based drugs, thalidomide containing PROTACs have now been developed using ligands designed to target multiple protein classes. In the case of both VHL- and CRBN-based PROTACS, disclosures have described the unpredictable nature of the both the targeting ligand (*Angew. Chem. Int. Ed.* 2016, 55, 807-810) as well as the linker (*J. Med. Chem.* 2017, 61, 583) in bringing about a ternary conformation of PROTAC, target protein and ubiquitin ligase that can facilitate protein degradation.

PROTACs engineered to degrade B-Raf would in principle confer certain advantages over conventional enzyme inhibitors, chief amongst them the inhibition of protein functions not achievable by an enzymatic inhibitor. In addition to catalyzing the phosphorylation of MEK, RAF family members function as allosteric regulators of their own catalysis function through the ability of their kinase domains to dimerize. This specific function underpins many of the limitations of current Raf inhibitors including acquired and intrinsic resistance.

The role of over-activation of the MAPK pathway in driving tumor progression, the availability of numerous potent small molecule ligands targeting this pathway, as well as the potential advantages of PROTACS in deactivating certain targets of interest have all combined to spur efforts to develop PROTACS targeting the intracellular degradation of various kinases in the MAPK pathway. In U.S. Pat. No. 9,938,264, Arvinas disclosed the use of PROTACS comprised of a tyrosine kinase inhibitor (TKI), a linker, and a CRBL or VHL ligand wherein the TKI included was selected from among known kinase inhibitors. In U.S. patent application no. 2018/0179183, Arvinas disclosed a series of PROTACS incorporating various inhibitors that target mutant V600E B-Raf kinase.

SUMMARY

It has been surprisingly shown herein that compounds of the application containing a pomalidomde E3 ubiquitin ligase binding moiety linked to a BI-882370 Raf protein kinase binding moiety display activity in inhibiting and/or degrading B-Raf V600E protein in tumor cell lines. Comparable compounds comprising thalidomide as the E3 ubiquitin ligase binding moiety and/or dabrafenib as the Raf protein kinase binding moiety did not display any B-Raf V600E protein degradation activity in the same tumor cell lines and under similar conditions, highlighting the surprising results obtained with the compounds of the application.

Accordingly, the present application includes a compound of Formula I or a pharmaceutically acceptable salt and/or solvate thereof:

wherein

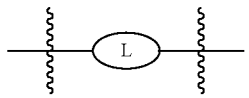

is a linker group, and

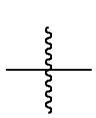

represents a point of covalent attachment.

In an embodiment,

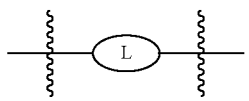

comprises at least one $C_{1-14}$alkylene, optionally interrupted by one or more heteromoieties selected from O, S, and NR and optionally interrupted by one or two amides and/or one triazole, wherein R is $C_{1-4}$alkyl.

In an embodiment,

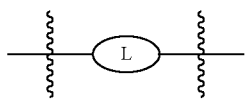

I

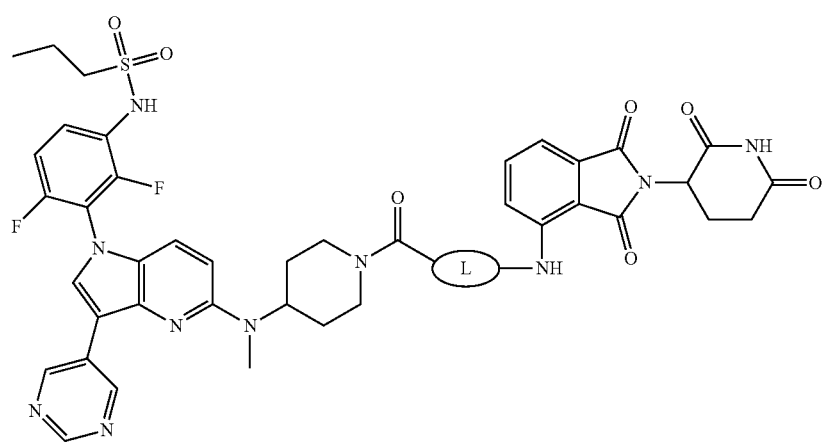

is a group of Formula II:

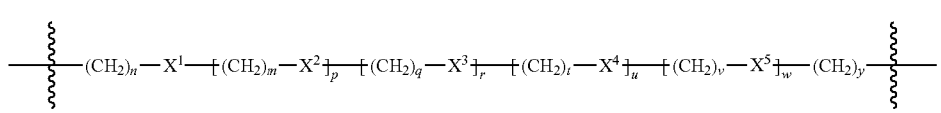

wherein

represents a point of covalent attachment;
$X^1$ is O, S, NR, C(O)NH or $CH_2$;
$X^2$ is O, S or NR;
$X^3$ is O, S, NR or triazole;
$X^4$ is O, S or NR;
$X^5$ is O, S, NR or C(O)NH;
n and y are integers independently selected from 1 to 6;
m, q, t, and v are integers independently selected from 1 to 3;
p and u are integers independently selected from 0 to 14;
r and w are independently 0 or 1; and
R is $C_{1-4}$alkyl.

In an embodiment, the present application includes a composition comprising one or more compounds of the application and a carrier.

The present application also includes a method for inhibiting and/or degrading V600E mutant B-Raf in a cell, either in a biological sample or in a patient, comprising administering an effective amount of one or more compounds of the application to the cell.

The present application also includes a method of treating a disease, disorder or condition that is mediated or treatable by inhibiting and/or degrading V600E mutant B-Raf protein comprising administering a therapeutically effective amount of one or more compounds of the application to a subject in need thereof.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole

BRIEF DESCRIPTION OF DRAWINGS

The embodiments of the application will now be described in greater detail with reference to the attached drawings in which.

DETAILED DESCRIPTION

I. Definitions

Figure 1:
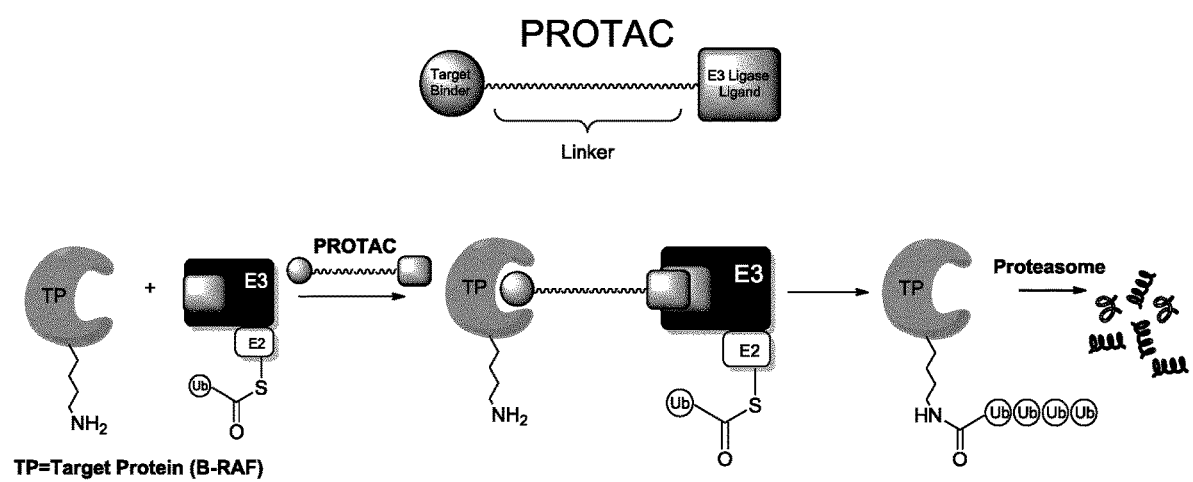
FIG. 1 is a schematic illustrating the concept of a PROTAC targeting mutant B-Raf.

Unless otherwise indicated, the definitions and embodiments described in this and other sections are intended to be applicable to all embodiments and aspects of the present application herein described for which they are suitable as would be understood by a person skilled in the art.

The term "compound(s) of the application" or "compound(s) of the present application" and the like as used herein refers to a compound of Formula I or pharmaceutically acceptable salts and/or solvates thereof.

The term "composition(s) of the application" or "composition(s) of the present application" and the like as used herein refers to a composition, such a pharmaceutical composition, comprising one or more compounds of the application.

The term "and/or" as used herein means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the application exist as individual salts and hydrates, as well as a combination of, for example, a solvate of a salt of a compound of the application.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

The present description refers to a number of chemical terms and abbreviations used by those skilled in the art. Nevertheless, definitions of selected terms are provided for clarity and consistency.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The term "alkyl" as used herein, whether it is used alone or as part of another group, means straight or branched chain, saturated alkyl groups. The number of carbon atoms that are possible in the referenced alkyl group are indicated by the prefix "$C_{n1-n1}$". For example, the term $C_{1-10}$alkyl means an alkyl group having 1, 2, 3, 4, 5, 6, 7, 8, 9 or 10 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms.

The term "triazole" as used herein refers to a heterocyclic group with molecular formula $C_2H_3N_3$, having a five-membered ring comprised of two carbon atoms and three nitrogen atoms and two double bonds, and including isomers and tautomers thereof.

The term "available", as in "available hydrogen atoms" or "available atoms" refers to atoms that would be known to a person skilled in the art to be capable of replacement by a substituent.

The term "amine" or "amino," as used herein, whether it is used alone or as part of another group, refers to groups of the general formula NR'R", wherein R' and R" are each independently selected from hydrogen or $C_{1-6}$alkyl.

The term "atm" as used herein refers to atmosphere.

The term "MS" as used herein refers to mass spectrometry.

The term "aq." as used herein refers to aqueous.

DCM as used herein refers to dichloromethane.

DIPEA as used herein refers to N,N-diisopropyl ethylamine

DMF as used herein refers to dimethylformamide.

DMSO as used herein refers to dimethylsulfoxide.

EtOAc as used herein refers to ethyl acetate.

HATU as used herein refers to 1-[Bis(dimethylamino)methylene]-1H-1,2,3-triazolo[4,5-b]pyridinium 3-oxid hexafluorophosphate, or hexafluorophosphate azabenzotriazole tetramethyl uranium.

MeOH as used herein refers to methanol.

MeCN as used herein refers to acetonitrile.

HCl as used herein refers to hydrochloric acid.

TFA as used herein refers to trifluoroacetic acid.

TBAF as used herein refers to tetra-n-butylammonium fluoride.

CsF as used herein is cesium fluoride.

μwave as used herein refers to a microwave reaction vessel.

SnAr as used herein represents nucleophilic aromatic substitution.

LCMS as used herein refers to liquid chromatography-mass spectrometry.

HEPES as used herein refers to 4-(2-hydroxyethyl)-1-piperazineethanesulfonic acid.

EDTA as used herein refers to ethylenediaminetetraacetic acid.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J.F.W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "subject" as used herein includes all members of the animal kingdom including mammals, and suitably refers to humans. Thus the methods and uses of the present application are applicable to both human therapy and veterinary applications.

The term "pharmaceutically acceptable" means compatible with the treatment of subjects.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound.

A base addition salt suitable for, or compatible with, the treatment of subjects is any non-toxic organic or inorganic base addition salt of any acidic compound.

The term "solvate" as used herein means a compound, or a salt of a compound, wherein molecules of a suitable solvent are incorporated in the crystal lattice The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations.

"Palliating" a disease, disorder or condition means that the extent and/or undesirable clinical manifestations of a disease, disorder or condition are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

The term "disease, disorder or condition" as used herein refers to a disease, disorder or condition mediated or treatable by inhibiting and/or degrading V600E mutant B-Raf protein, such as by a compound of the application.

The term "mediated or treatable by inhibition and/or degradation of V600E mutant B-Raf" as used herein means that the disease, disorder or condition to be treated is affected by, modulated by and/or has some biological basis, either direct or indirect, that includes the presence in a cell of V600E mutated B-Raf protein. Such biological basis includes, for example, proteins that are products of or precursors to mutant B-Raf and/or products of mutant V600E B-Raf gene expression. In a refined context, "inhibition and/or degradation of V600E mutant B-Raf" refers to an effect mediated through inhibition of the signaling in a cell mutant by V600E mutated B-Raf. In a broader context, "inhibition and/or degradation of V600E mutant B-Raf" can include the large number of diseases that are caused by aberrant signaling due to the presence of V600E mutated B-Raf in a cell, including tumor cells.

The term "Raf binder" or "Raf binding moiety" as used herein refers to a compound that binds to Raf enzyme and said binding modulates, for example, decreases, Raf activity. In an embodiment, the Raf enzyme is a V600E mutated B-Raf enzyme.

The term "BI-882370" as used herein refers to a compound having the IUPAC name: N-[3-[5-[(1-ethylpiperidin-4-yl)-methylamino]-3-pyrimidin-5-ylpyrrolo[3,2-b]pyridine-1-yl]-2,4-difluorophenyl]propane-1-sulfonamide, and having the chemical formula:

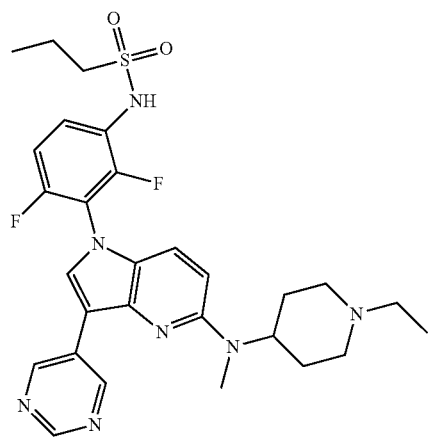 [SMILES: CCCS(=O)(=O)Nc1ccc(F)c(-n2cc(-c3cncnc3)c3nc(N(C)C4CCN(CC)CC4)ccc32)c1F]

The term "linker group" as used herein refers to any molecular structure that joins two or more other molecular structures together.

The term "BI-882370-linker" as used herein refers to BI-882370 or BI-882370 derivative that has been covalently attached to a linker group.

The term "E3 ubiquitin ligase binding compound" as used herein refers to a compound that binds to E3 ubiquitin ligase and/or E3 ubiquitin ligase complex and promotes ubiquitination.

The term "pomalidomide" as used herein refers to a compound having the IUPAC name: 4-Amino-2-(2,6-dioxo-3-piperidinyl)-1H-isoindole-1,3(2H)-dione and having the chemical formula:

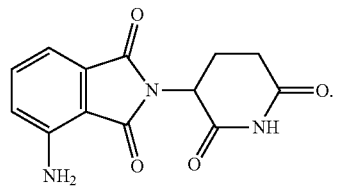 [SMILES: Nc1cccc2c1C(=O)N(C1CCC(=O)NC1=O)C2=O]

The term "pomalidomide-linker" as used herein refers to pomalidomide or pomalidomide derivative that has been covalently attached to a linker group.

The term "degradation" as used herein refers to any decrease in the amount of V600E mutated B-Raf protein, for example as measured by Western Blot, in the presence of one or more compounds of the application compared to a control, (for example, otherwise identical conditions except in the absence of one or more compounds of the application).

The term "inhibit" or "inhibition" as used herein refers to any decrease in an enzyme's activity in the presence of one or more compounds of the application compared to a control (for example, otherwise identical conditions except for the absence of one of more compounds of the application). For example, the enzyme activity is the activity of V600E mutated B-Raf, for example, as measured by the decrease in the phosphorylation of downstream effectors of B-Raf including MEK and ERK.

As used herein, the term "effective amount" or "therapeutically effective amount" means an amount of one or more compounds of the application that is effective, at dosages and for periods of time necessary to achieve the desired result. For example in the context of treating a disease, disorder or condition mediated or treatable by inhibition and/or degradation of V600E mutant B-Raf, an effective amount is an amount that, for example, increases said inhibition compared to the inhibition and/or degradation without administration of the one or more compounds.

The term "administered" as used herein means administration of a therapeutically effective amount of one or more compounds or compositions of the application to a cell, tissue, organ or subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder.

The term "cancer" as used herein refers to cellular-proliferative disease states.

II. Compounds and Compositions of the Application

It has been surprisingly shown herein that compounds of the application containing a pomalidomide E3 ubiquitin ligase binding moiety linked to a BI-882370 Raf protein kinase binding moiety display activity in inhibiting and/or degrading B-Raf V600E protein in tumor cell lines. Comparable compounds comprising thalidomide as the E3 ubiquitin ligase binding moiety and/or dabrafenib as the Raf protein kinase binding moiety did not display any B-Raf V600E protein degradation activity in the same tumor cell lines and under similar conditions, highlighting the surprising results obtained with the compounds of the application.

Accordingly, the present application includes a compound of Formula I or a pharmaceutically acceptable salt and/or solvate thereof:

wherein is a linker group, and represents a point of covalent attachment.

In an embodiment, comprises at least one $C_{1-14}$alkylene, optionally interrupted by one or more heteromoieties selected from O, S, and NR and optionally interrupted by one or two amides and/or one triazole, wherein R is $C_{1-4}$alkyl.

A person of skill in the art would appreciate that the linker should have a length and spatial orientation appropriate to link the E3 ubiquitin ligase binding moiety with the Raf protein binding moiety and allow the E3 ubiquitin ligase to tag the Raf protein for degradation.

In an embodiment,

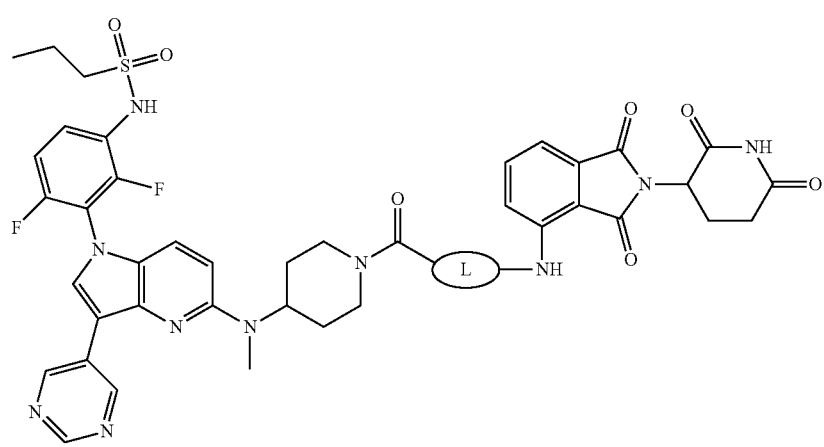

I is a group of Formula II:

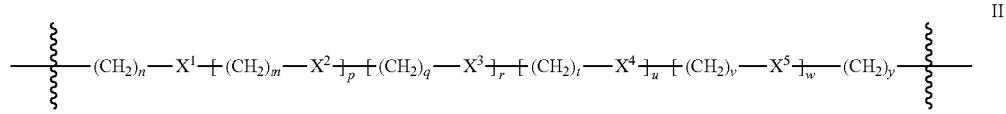

wherein

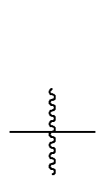

represents a point of covalent attachment;

$X^1$ is O, S, NR, C(O)NH or $CH_2$;

$X^2$ is O, S or NR;

$X^3$ is O, S, NR or triazole;

$X^4$ is O, S or NR;

$X^5$ is O, S, NR or C(O)NH;

n and y are integers independently selected from 1 to 6;

m, q, t, and v are integers independently selected from 1 to 3;

p and u are integers independently selected from 0 to 14;

r and w are independently 0 or 1, and

R is $C_{1-4}$alkyl.

In an embodiment, m, q, t, and v are 2. In an embodiment, n and y are integers independently selected from 1 to 4. In an embodiment, n and y are independently 2 or 3. In an embodiment, n and y are both 2.

In an embodiment, $X^1$, $X^2$, $X^3$, $X^4$ and/or $X^5$ are/is O. In an embodiment, $X^1$, $X^2$, $X^3$, $X^4$ or $X^5$ are O.

In an embodiment, r, u or w are 0. In an embodiment, r, u and w are 0.

In an embodiment, p is an integer selected from 1-8. In an embodiment, p is an integer selected from 2-4. In an embodiment, p is 3.

In an embodiment

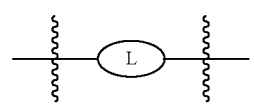

is a group of Formula III:

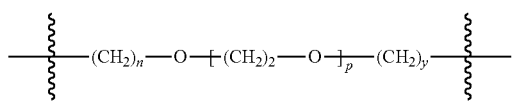

wherein

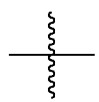

represents a point of covalent attachment;

n and y are integers independently selected from 1 to 6; and p is an integer selected from 0 to 14.

In an embodiment, n and y are independently 2 or 3 and p is selected from 1-8.

In an embodiment, $X^3$ is triazole. In an embodiment, $X^3$ is 1,2,3-triazole. In an embodiment, r is 1.

In an embodiment,

is a group of Formula IV:

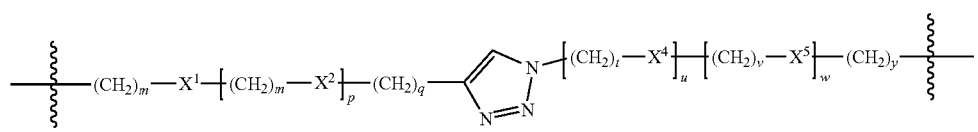

wherein

[structure: point of covalent attachment]

represents a point of covalent attachment;

$X^1$ is O, S, NR, C(O)NH or $CH_2$;

$X^2$ is O, S or NR;

$X^4$ is O, S or NR;

$X^5$ is O, S, NR or C(O)NH;

n and y are integers independently selected from 1 to 6;

m, q, t, and v are integers independently selected from 1 to 3;

p and u are integers independently selected from 0 to 14;

w is 0 or 1, and

R is $C_{1-4}$alkyl.

In an embodiment, $X^1$ is C(O)NH. In an embodiment, w is 0.

In an embodiment,

[structure with L]

is a group of Formula V:

$$\text{structure V: } -(CH_2)_n-C(O)-NH-[(CH_2)_m-X^2]_p-[(CH_2)_q-X^3]_u-(CH_2)_y-$$

wherein

[structure: point of covalent attachment]

represents a point of covalent attachment;

$X^2$ is O, S or NR;

$X^3$ is O, S, NR or triazole;

n and y are integers independently selected from 1 to 6;

m and q are integers independently selected from 1 to 3;

p and u are integers independently selected from 0 to 14; and

R is $C_{1-4}$alkyl.

In an embodiment, $X^2$ and $X^3$ are O.

In an embodiment,

[structure with L]

is selected from the groups listed below:

[PEG3 structure]

[PEG4 structure]

[PEG5 structure]

[PEG6 structure]

[PEG7 structure]

[PEG with amide linker structure]

[amide-PEG structure], and

[PEG-triazole-PEG structure].

In an embodiment, the compound of Formula I is selected from the compounds listed below:

| Compound I.D | Example # | Structures |
|---|---|---|
| I-1 | 1 | 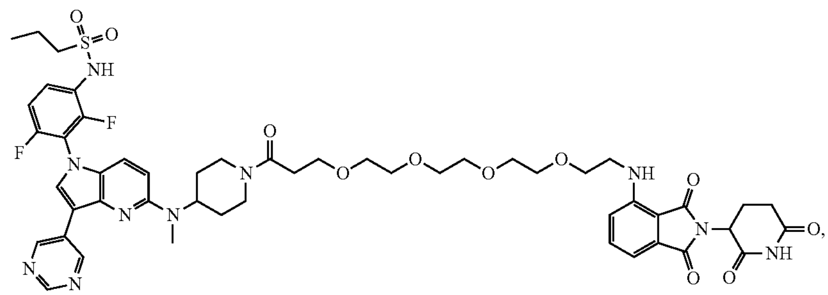 [SMILES: CCCS(=O)(=O)Nc1ccc(F)c(-n2cc(-c3cncnc3)c3nc(N(C)C4CCN(C(=O)CCOCCOCCOCCOCCNc5cccc6c5C(=O)N(C5CCC(=O)NC5=O)C6=O)CC4)ccc32)c1F] |
| I-2 | 2 | 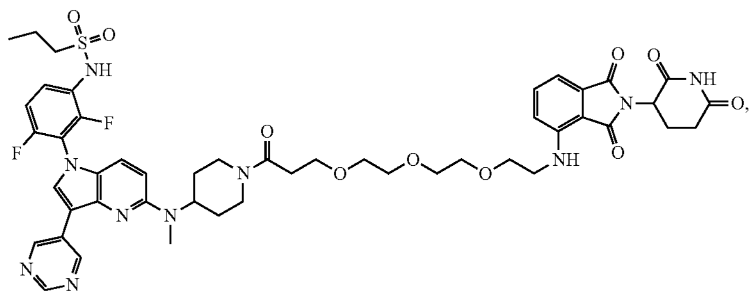 [SMILES: CCCS(=O)(=O)Nc1ccc(F)c(-n2cc(-c3cncnc3)c3nc(N(C)C4CCN(C(=O)CCOCCOCCOCCNc5cccc6c5C(=O)N(C5CCC(=O)NC5=O)C6=O)CC4)ccc32)c1F] |
| I-3 | 3 | 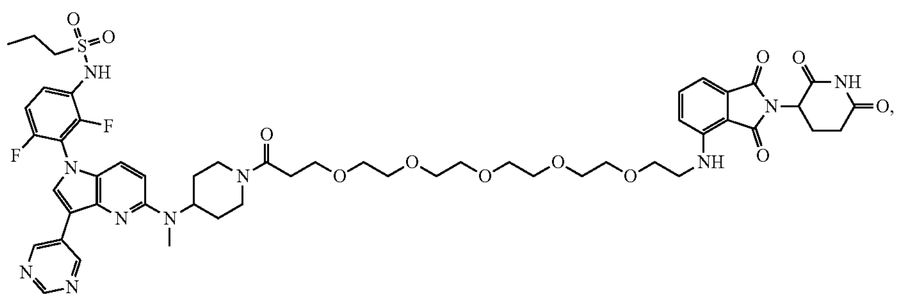 [SMILES: CCCS(=O)(=O)Nc1ccc(F)c(-n2cc(-c3cncnc3)c3nc(N(C)C4CCN(C(=O)CCOCCOCCOCCOCCOCCNc5cccc6c5C(=O)N(C5CCC(=O)NC5=O)C6=O)CC4)ccc32)c1F] |
| I-4 | 4 | 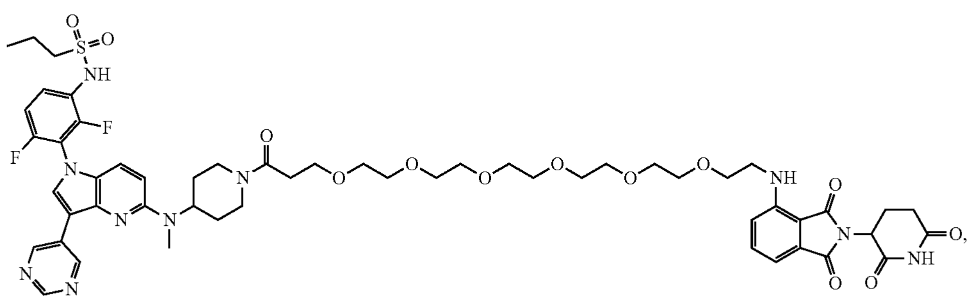 [SMILES: CCCS(=O)(=O)Nc1ccc(F)c(-n2cc(-c3cncnc3)c3nc(N(C)C4CCN(C(=O)CCOCCOCCOCCOCCOCCOCCNc5cccc6c5C(=O)N(C5CCC(=O)NC5=O)C6=O)CC4)ccc32)c1F] |
| I-5 | 5 | 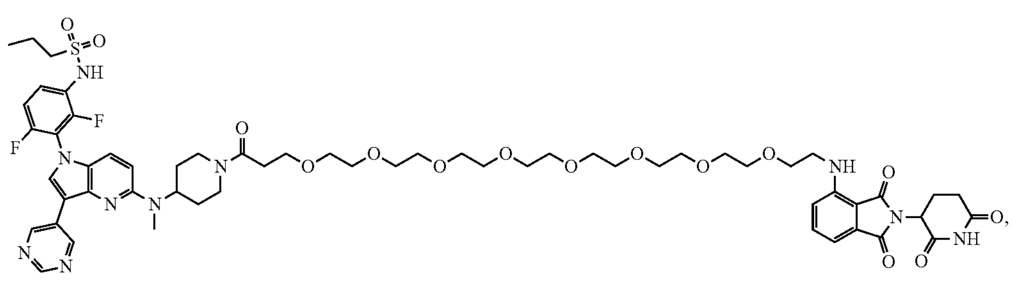 |

| Compound I.D | Example # | Structures |
|---|---|---|
| I-6 | 6 | (structure image) | or a pharmaceutically acceptable salt and/or solvate thereof.

In an embodiment the pharmaceutically acceptable salt is an acid addition salt or a base addition salt. The selection of a suitable salt may be made by a person skilled in the art (see, for example, S. M. Berge, et al., "Pharmaceutical Salts," J. Pharm. Sci. 1977, 66, 1-19).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. The selection of the appropriate salt may be useful, for example, so that an ester functionality, if any, elsewhere in a compound is not hydrolyzed. The selection criteria for the appropriate salt will be known to one skilled in the art.

Solvates of compounds of the application include, for example, those made with solvents that are pharmaceutically acceptable. Examples of such solvents include water (resulting solvate is called a hydrate) and ethanol and the like. Suitable solvents are physiologically tolerable at the dosage administered.

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier. In embodiments of the application the pharmaceutical compositions are used in the treatment of any of the diseases, disorders or conditions described herein.

The compounds of the application are administered to a subject in a variety of forms depending on the selected route of administration, as will be understood by those skilled in the art. For example, a compound of the application is administered by oral, inhalation, parenteral, buccal, sublingual, nasal, rectal, vaginal, patch, pump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a compound of the application is orally administered, for example, with an inert diluent or with an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

In some embodiments, a compound of the application is administered parenterally. For example, solutions of a compound of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiment, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, a compound of the application is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels and powders. For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein a compound of the application is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to theobroma oil (also known as cocoa butter), glycerinated gelatin, other glycerides, hydrogenated vegetable oils, mixtures of polyethylene glycols of various molecular weights and fatty acid esters of polyethylene glycol. See, for example: Remington's Pharmaceutical Sciences, 16th Ed., Mack Publishing, Easton, PA, 1980, pp. 1530-1533 for further discussion of suppository dosage forms.

In some embodiments a compound of the application is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the application is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

A compound of the application including pharmaceutically acceptable salts and/or solvates thereof is suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

III. Methods and Uses of the Application

The compounds of the application have been shown to inhibit and/or degrade V600E mutant B-Raf protein.

Accordingly, the present application includes a method for inhibiting and/or degrading V600E mutant B-Raf in a cell, either in a biological sample or in a patient, comprising administering an effective amount of one or more compounds of the application to the cell. The application also includes a use of one or more compounds of the application for inhibiting and/or degrading V600E mutant B-Raf in a cell as well as a use of one or more compounds of the application for the preparation of a medicament for inhibiting and/or degrading V600E mutant B-Raf in a cell. The application further includes one or more compounds of the application for use to inhibit and/or degrade V600E mutant B-Raf in a cell.

As the compounds of the application have been shown to be capable of inhibiting and/or degrading V600E mutant B-Raf protein, the compounds of the application are useful for treating diseases, disorders or conditions mediated or treatable by inhibiting and/or degrading V600E mutant B-Raf protein. Therefore the compounds of the present application are useful as medicaments. Accordingly, the present application includes a compound of the application for use as a medicament.

The present application also includes a method of treating a disease, disorder or condition that is mediated or treatable by inhibiting and/or degrading V600E mutant B-Raf protein comprising administering a therapeutically effective amount of one or more compounds of the application to a subject in need thereof.

The present application also includes a use of one or more compounds of the application for treating a disease, disorder or condition mediated or treatable by inhibiting and/or degrading V600E mutant B-Raf as well as a use of one or more compounds of the application for the preparation of a medicament for treating of a disease, disorder or condition mediated or treatable by inhibiting and/or degrading V600E mutant B-Raf protein. The application further includes one or more compounds of the application for use in treating a disease, disorder or condition mediated or treatable by inhibiting and/or degrading V600E mutant B-Raf.

In an embodiment, the disease, disorder or condition mediated or treatable by inhibiting and/or degrading V600E mutant B-Raf protein is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

Neoplasms can be benign (such as uterine fibroids and melanocytic nevi), potentially malignant (such as carcinoma in situ) or malignant (i.e. cancer). Exemplary neoplastic disorders include the so-called solid tumours and liquid tumours, including but not limited to carcinoma, sarcoma, metastatic disorders (e.g., tumors arising from the prostate), hematopoietic neoplastic disorders, (e.g., leukemias, lymphomas, myeloma and other malignant plasma cell disorders), metastatic tumors and other cancers.

In another embodiment of the present application, the disease, disorder or condition mediated or treatable by inhibiting and/or degrading V600E mutant B-Raf and its binding partners is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In an embodiment, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood;

Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

In an embodiment, the cancer is one that is impacted or mediated by mutations in the RAS-RAF-ERK signaling pathway. In an embodiment, the cancer is one that is impacted or mediated by mutations in b-Raf.

In an embodiment, the cancer is selected from melanoma, non small cell lung cancer, glioma, thyroid cancer and colorectal cancer.

In an embodiment, the disease, disorder or condition mediated or treatable by inhibiting and/or degrading V600E mutant B-Raf protein is a disease, disorder or condition associated with an uncontrolled and/or abnormal cellular activity affected directly or indirectly V600E mutant B-Raf protein. In another embodiment, the uncontrolled and/or abnormal cellular activity that is affected directly or indirectly by inhibiting and/or degrading V600E mutant B-Raf in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

The present application also includes a method of inhibiting uncontrolled and/or abnormal cellular activities mediated directly or indirectly by V600E mutant B-Raf protein, either in a biological sample or in a subject, comprising administering an effective amount of one or more compounds of the application to the cell. The application also includes a use of one or more compounds of the application for inhibition of uncontrolled and/or abnormal cellular activities mediated directly or indirectly by signaling of V600E mutant B-Raf protein in a cell as well as a use of one or more compounds of the application for the preparation of a medicament for inhibition of uncontrolled and/or abnormal cellular activities mediated directly or indirectly by V600E mutant B-Raf protein signaling in a cell. The application further includes one or more compounds of the application for use in inhibiting uncontrolled and/or abnormal cellular activities mediated directly or indirectly by aberrant V600E mutant B-Raf signaling in a cell.

In further embodiments, the present application also includes a method of treating a disease, disorder or condition that is mediated or treatable by inhibiting and/or degrading V600E mutant B-Raf protein comprising administering a therapeutically effective amount of one or more compounds of the application in combination with another known agent useful for treatment of a disease, disorder or condition mediated or treatable by inhibiting and/or degrading V600E mutant B-Raf protein to a subject in need thereof. The present application also includes a use of one or more compounds of the application in combination with a known agent useful for treatment of a disease, disorder or condition mediated or treatable by inhibiting and/or degrading V600E mutant B-Raf protein, for treatment of a disease, disorder or condition mediated or treatable by inhibiting and/or degrading V600E mutant B-Raf protein.

In a further embodiment, the disease, disorder or condition mediated or treatable by inhibiting and/or degrading V600E mutant B-Raf protein is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase and serine-threonine kinase inhibitors, immunotherapy, hormonal therapy and anti-angiogenic therapies.

In an embodiment, effective amounts vary according to factors such as the disease state, age, sex and/or weight of the subject. In a further embodiment, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated, and the like, but can nevertheless be routinely determined by one skilled in the art.

In an embodiment, the compounds of the application are administered at least once a week. However, in another embodiment, the compounds are administered to the subject from about one time per two weeks, three weeks or one month. In another embodiment, the compounds are administered about one time per week to about once daily. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

In an embodiment, the subject is a mammal. In another embodiment, the subject is human.

Compounds of the application are either used alone or in combination with other known agents useful for treating diseases, disorders or conditions that are mediated or treatable by inhibition and/or degradation of V600E mutant B-Raf protein, and those that are treatable with a B-Raf degrading agent, such as the compounds disclosed herein. When used in combination with other agents useful in treating diseases, disorders or conditions mediated or treatable by inhibition and/or degradation of V600E mutant B-Raf protein, it is an embodiment that a compound of the application is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application, an additional therapeutic agent, and a pharmaceutically acceptable carrier.

The dosage of a compound of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a compound of the application is administered initially in a suitable dosage that is adjusted as required, depending on the clinical response. Dosages will generally be selected to maintain a serum level of the compound of the application from about 0.01 µg/cc to about 1000 µg/cc, or about 0.1 µg/cc to about 100 µg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or 0.1 mg/kg to about 1 mg/kg.

IV. Methods of Preparing the Compounds of the Application

Compounds of the present application can be prepared by various synthetic processes. The choice of particular structural features and/or substituents may influence the selection of one process over another. The selection of a particular process to prepare a given compound of Formula I is within the purview of the person of skill in the art. Some starting materials for preparing compounds of the present application are available from commercial chemical sources. Other starting materials, for example as described below, are readily prepared from available precursors using straightforward transformations that are well known in the art. In the Schemes below showing the preparation of compounds of the application, all variables are as defined in Formula I, unless otherwise stated, In an embodiment, the compounds of Formula I are prepared as shown in Scheme 1. Therefore, a compound of Formula A, wherein the B-Raf inhibitor is BI-882370 and $FG_1$ is a first functional group, is coupled to a pomalido-mide-linker compound of Formula B, in which $FG_2$ is a second functional group attached to linker group

and $FG_1$ and $FG_2$ are selected such that they react to form a covalent bond to produce a compound of Formula I.

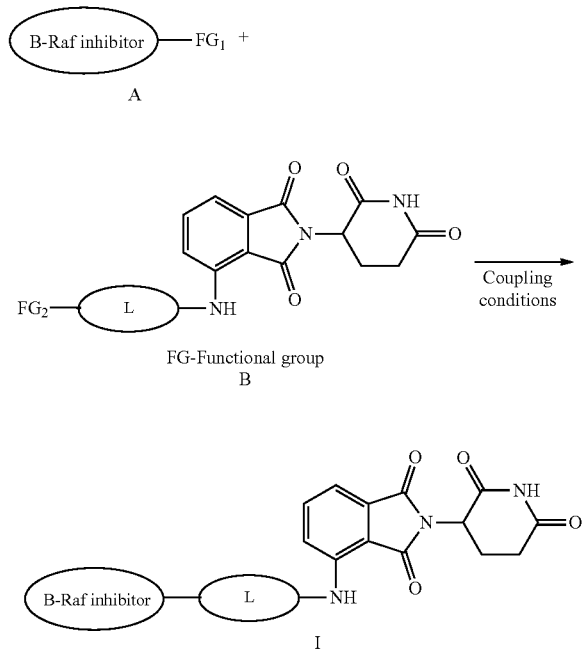

In an embodiment, compounds of Formula I are prepared as shown in Scheme 2. Therefore, an appropriate pomalidomide or pomalidomide derivative of Formula C, in which X is a suitable leaving group such as fluoride, is coupled with an appropriate bifunctional compound Formula D, in which $FG_3$ and $FG_4$ are appropriate functional groups, in the presence of a base such as 4-(dimethylamino)pyridine (DMAP), a coupling agent such as 1,1-carbonyldiimidazole (CDI) and in a solvent such as dimethylformaide (DMF) and followed by deprotection if necessary to provide compounds of Formula E. In an embodiment, the compound of Formula D comprises a primary or secondary amino group ($FG_4$) attached at one end of the linker group and an unprotected or protected functional group ($FG_3$) attached to the opposite end. In the embodiment shown in Scheme 2, the compound of Formula D comprises a primary amino group ($FG_4$) and a protected carboxylic acid group ($FG_3$). The pomalidomide-linker of Formula E is then coupled with an appropriate BI-882370 or BI-882370 derivative (compound of Formula F) in the presence of a base such as N,N-diisopropylethylamine (DIPEA), a coupling agent such as hexafluorophosphate azabenzotriazole tetramethyl uronium (HATU) in a solvent such as DMF to yield the compound of Formula I. In the embodiment shown in Scheme 2, the BI-882370 derivative (compound of Formula F) is N-de-ethyl BI-882370.

Scheme 2

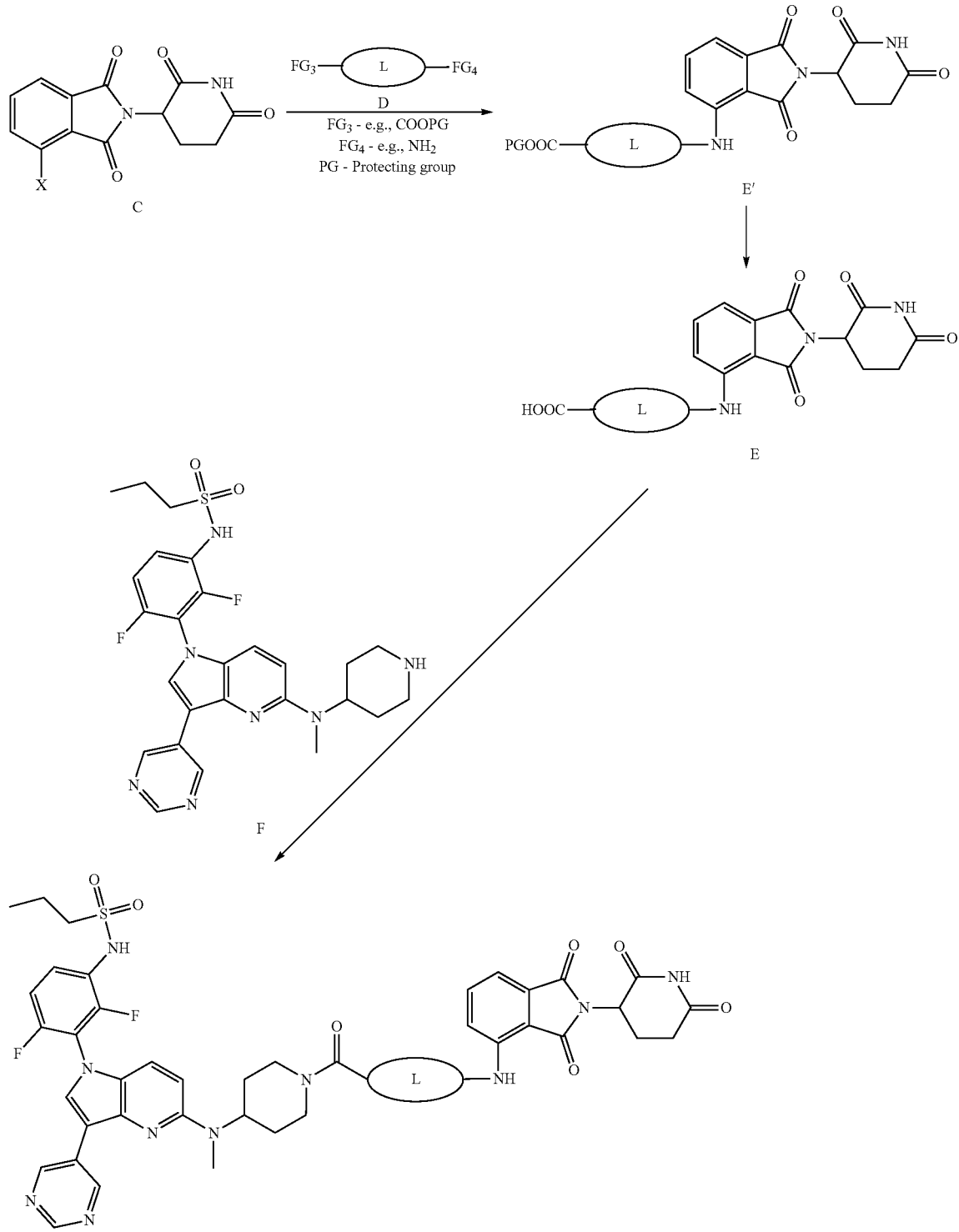

The pomalidomide or pomalidomide derivative (compound of formula C) can be synthesized through known methods, for example, using the synthetic procedures found in *Chemistry & Biology*, 2015, 22(6).

The BI-882370 derivative or BI-882370 (compound of Formula F) can be synthesized through known methods, for example, using the synthetic procedures described in PCT Patent Application publication no. WO2012/104388A1.

A person skilled in the art would appreciate that, in an alternate method for the preparation of the compound of Formula I, a suitable bifunctional compound of Formula D may be first reacted with a suitable BI-882370 derivative of Formula F, deprotected if necessary, and then coupled with pomalidomide or a suitable pomalidomide derivative of Formula C, to provide the compound of Formula I.

In some embodiments, when the linker comprises a triazole (i.e., $X^3$ is triazole), the triazole ring is incorporated in the linker group by reacting a suitable azide precursor compound with a suitable acetylene precursor compound using click reaction conditions (e.g., *Tetrahedron* 2016, 72, 5257-5283; *Tetrahedron* 2016, 72, 6136-6141).

The formation of a desired compound salt is achieved using standard techniques. For example, the neutral compound is treated with an acid or base in a suitable solvent and the formed salt is isolated by filtration, extraction or any other suitable method.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

EXAMPLES

The following non-limiting examples are illustrative of the present application.

General Methods

All oxygen and/or moisture sensitive reactions were carried out under a nitrogen atmosphere. Common reagents and laboratory grade solvents were purchased from commercial vendors and used as received, without further purification unless otherwise indicated. Flash Column Chromatography performed using a Teledyne ISCO Combiflash system fitted with a RediSep Rf Normal-phase Silica (60 Å mesh) 12-gram Flash Cartridge and RediSep Rf C18 Reversed-phase (60 Å mesh) 13-gram Flash Cartridge. The yields given refer to chromatographically purified and spectroscopically pure compounds, unless stated otherwise. $^1$H and $^{19}$F NMR spectra were recorded on a Bruker Avance-III 500 MHz spectrometer (500 MHz $^1$H, 471 MHz $^{19}$F) at room temperature. Chemical shifts were reported in ppm relative to the residual CDCl$_3$ (G 7.26 ppm 1H) or d6-DMSO (G 2.50 ppm $^1$H). NMR chemical shifts were expressed in ppm relative to internal solvent peaks, and coupling constants were measured in Hz. Data are reported as follows: chemical shifts (δ), multiplicity (br=broad, s=singlet, d=doublet, t=triplet, q=quartet, m=multiplet); coupling constant(s) (J) in Hz; integration. Unless otherwise noted, NMR data were collected at 25° C. Compound Purity Determination Conducted by UV absorbance at 254 nm during tandem liquid chromatography/mass spectrometry (LCMS) using a Waters Acquity separations module. Low Resolution Mass Spectrometry (LRMS) Conducted in positive ion mode using a Waters Acquity SQD mass spectrometer (electrospray ionization source) fitted with a PDA detector. Mobile phase A consisted of 0.1% formic acid in water, while mobile phase B consisted of 0.1% formic acid in acetonitrile. The gradient that was followed is presented in the table below.

| Time (min) | Flow (mL/min) | % A | % B |
| --- | --- | --- | --- |
| Initial | 0.4 | 90 | 10 |
| 1.8 | 0.4 | 5 | 95 |
| 2.3 | 0.4 | 5 | 95 |
| 2.5 | 0.4 | 90 | 10 |
| 3 | 0.4 | 90 | 10 |
| 5 | 0 | 90 | 10 |

Column 1: Acquity UPLC CSH C18 (2.1×50 mm, 130 Å, 1.7 μm. Part No. 186005296) or Column 2: Acquity UPLC BEH C8 (2.1×50 mm, 130 Å, 1.7 μm. Part No. 186002877). Both were used with column temperature maintained at 25° C. The sample solution injection volume was 1μ High Resolution Mass Spectrometry (HRMS) Conducted using a Waters Xevo quadrupole-time-of-flight (QTOF) hybrid mass spectrometer system coupled with an Acquity ultra-performance liquid chromatography (UPLC) system.

Chromatographic Separations carried out on an Acquity UPLC CSH C18 (2.1×50 mm, 130 Å, 1.7 μm. Part No. 186005296) or Column 2: Acquity UPLC BEH C8 (2.1×50 mm, 130 Å, 1.7 μm. Part No. 186002877). The mobile phase was 0.1% formic acid in water (solvent A) and 0.1% formic acid in acetonitrile (solvent B). MassLynx 4.1 was used for data analysis.

The compounds and/or intermediates were characterized by LCMS. General conditions are as follows. Low and High resolution Mass spectra were acquired on LC/MS systems using electrospray ionization methods from a range of instruments of the following configurations: Low resolution—Waters ACQUITY UPLC system with a SQ (single quadrupole) MS; Waters ACQUITY UPLC H-Class system with a 3100 (single quadrupole) MS. High resolution—Waters ACQUITY UPLC II system equipped with a Synapt Xevo QTof and Waters ACQUITY UPLC II system equipped with a Synapt G2S QTof mass spectrometer with an atmospheric pressure ionization source. [M+H] refers to the protonated molecular ion of the chemical species.

Nuclear magnetic resonance (NMR) analysis was performed on a Bruker 500 MHz NMR spectrometer using ICON-NMR, under TopSpin program control. Spectra were measured at 298K, unless indicated otherwise and were referenced relative to the solvent chemical shift.

The following compounds were prepared using one or more of the synthetic methods outlined in Schemes 1 to 2:

Example 1

N-(3-(5-((1-(1-((2-(2,6-dioxopiperidin-3-yl)-1,3-dioxoisoindolin-4-yl)amino)-3,6,9,12-tetraoxapentadecan-15-oyl)piperidin-4-yl)(methyl)amino)-3-(pyrimidin-5-yl)-1H-pyrrolo[3,2-b]pyridin-1-yl)-2,4-difluorophenyl)propane-1-sulfonamide (I-1)

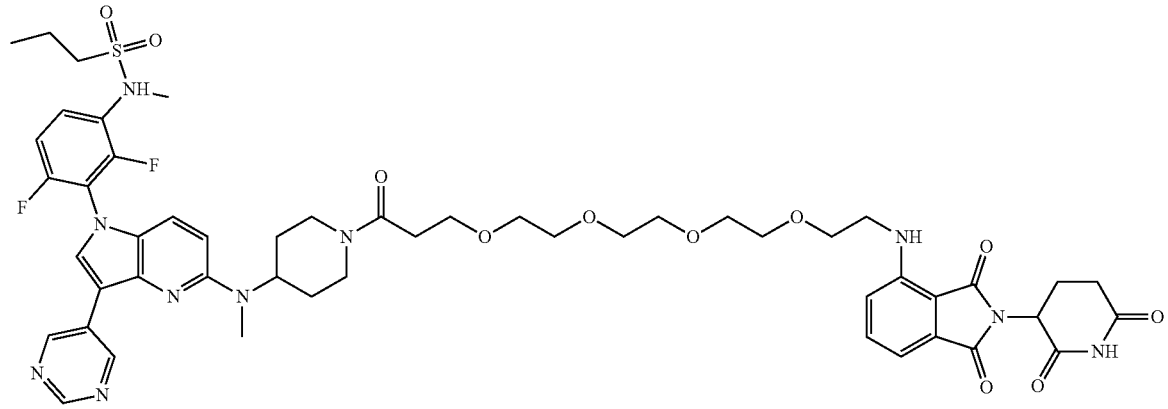 [SMILES: CCCS(=O)(=O)N(C)c1ccc(F)c(-n2cc(-c3cncnc3)c3nc(N(C)C4CCN(C(=O)CCOCCOCCOCCOCCNc5cccc6c5C(=O)N(C5CCC(=O)NC5=O)C6=O)CC4)ccc32)c1F]

Step 1: 5-amino-2-(4-fluoro-1,3-dioxoisoindolin-2-yl)-5-oxopentanoic acid (2)

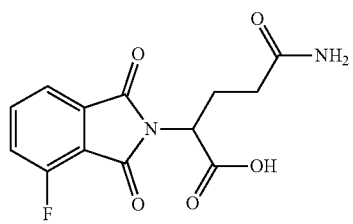 [SMILES: NC(=O)CCC(C(=O)O)N1C(=O)c2cccc(F)c2C1=O]

The procedure followed was similar to that described in (*Chemistry & Biology*, 2015, 22(6), 755-763). To a solution of 3-fluorophthalic anhydride (8.81 g, 53.0 mmol) in dry N,N-dimethylformamide (DMF) (50 ml) L-glutamine (10 g, 68.4 mmol) was added at RT. The reaction mixture was stirred at 100° C. overnight. The solvent was removed under reduced pressure and the residue was stirred overnight in 6N HCl (50 mL) at rt. The resulting precipitation was collected by filtration, washed with water and dried to afford 11.4 g 5-amino-2-(4-fluoro-1,3-dioxoisoindolin-2-yl)-5-oxopentanoic acid (36.8 mmol, 69.4% yield). $^1$H NMR (500 MHz, DMSO-$d_6$): δ 7.91-7.97 (m, 1H), 7.70-7.80 (m, 2H), 7.20 (br. s., 1H), 6.72 (br. s., 1H), 4.75 (dd, J=4.52, 10.88 Hz, 1H), 2.21-2.39 (m, 2H), 2.07-2.17 (m, 2H). $^{19}$F NMR (471 MHz, DMSO $d_6$): δ −114.82 (s, 1F). LCMS (ES$^+$): m/z 295.34 [M+1]$^+$.

Step 2. 2-(2,6-dioxopiperidin-3-yl)-4-fluoroisoindoline-1,3-dione (3)

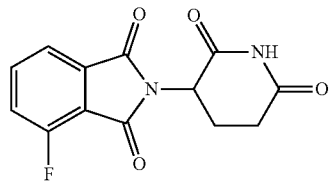 [SMILES: O=C1CCC(N2C(=O)c3cccc(F)c3C2=O)C(=O)N1]

A mixture of 5-amino-2-(4-fluoro-1,3-dioxoisoindolin-2-yl)-5-oxopentanoic acid (5.7 g, 19.37 mmol), 1,1'-carbonyldiimidazole (3.72 g, 22.94 mmol), 4-(dimethylamino)pyridine (200 mg, 1.637 mmol) in acetonitrile (23 ml) was refluxed overnight. The reaction mixture was evaporated with a Celite® and purified using an ISCO Combiflash apparatus (normal phase silica gel) eluting with DCM-MeOH (0% to 100% MeOH). The desired fractions were collected, concentrated and dried on the rotavap to afford 1.1 g of 2-(2,6-dioxopiperidin-3-yl)-4-fluoroisoindoline-1,3-dione (3.78 mmol, 19.53% yield). $^1$H NMR (500 MHz, CDCl$_3$: δ 8.11 (br. s., 1H), 7.71-7.81 (m, 2H), 7.44 (t, J=8.44 Hz, 1H), 5.00 (dd, J=5.38, 12.47 Hz, 1H), 2.73-2.96(m, 3H), 2.14-2.21 (m, 1H). $^{19}$F NMR (471 MHz, CDCl$_3$): δ −111.69 (s, 1F). LCMS (ES$^+$): m/z 277.30 [M+1]$^+$.

Step 3: Tert-butyl 1-((2-(2,6-dioxopiperidin-3-yl)-1,3-dioxoisoindolin-4-yl)amino)-3,6,9,12-tetraoxapentadecan-15-oate

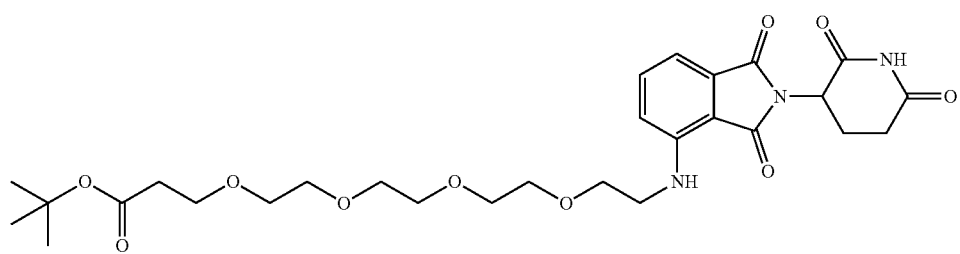 [SMILES: CC(C)(C)OC(=O)CCOCCOCCOCCOCCNc1cccc2c1C(=O)N(C1CCC(=O)NC1=O)C2=O]

A mixture of tert-butyl 1-amino-3,6,9,12-tetraoxapentadecan-15-oate (384 mg, 1.195 mmol), N,N-diisopropylethylamine (421 mg, 3.26 mmol) and 242,6-dioxopiperidin-3-yl)-4-fluoroisoindoline-1,3-dione (300 mg, 1.086 mmol) in 1,4-dioxane (12 mL) was stirred at 90° C. overnight. The reaction mixture was evaporated with a Celite® and purified using an ISCO Combiflash (normal phase silica gel) eluting with DCM-Acetonitrile (0% to 100% DCM). The desired fractions were collected, concentrated and dried on the rotavap to afford the tert-butyl 1-((2-(2,6-dioxopiperidin-3-yl)-1,3-dioxoisoindolin-4-yl)amino)-3,6,9,12-tetraoxapentadecan-15-oate (137 mg, 22%). $^1$H NMR (500 MHz, CDCl$_3$) δ 8.14 (br. s., 1H), 7.42 (dd, J=7.34, 8.31 Hz, 1H), 7.04 (d, J=7.09 Hz, 1H), 6.86 (d, J=8.56 Hz, 1H), 6.34-6.49 (m, 1H), 4.85 (s, 1H), 3.53-3.66 (m, 19H), 3.36-3.45 (m, 2H), 2.69 (s, 3H), 2.40-2.47 (m, 2H), 1.99-2.11 (m, 1H), 1.36-1.38 (m, 10H). LCMS (ES$^+$): m/z 578.46 [M+1]$^+$.

Step 4: 1-((2-(2,6-Dioxopiperidin-3-yl)-1,3-dioxoisoindolin-4-yl)amino)-3,9,12-tetraoxapentadecan-15-oic acid

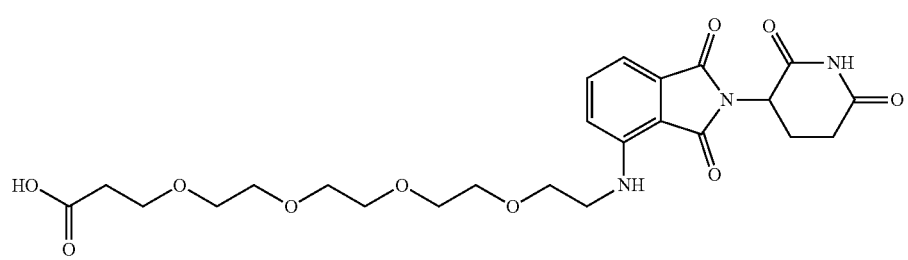 [SMILES: O=C(O)CCOCCOCCOCCOCCNc1cccc2c1C(=O)N(C1CCC(=O)NC1=O)C2=O]

The tert-butyl 1-((2-(2,6-dioxopiperidin-3-yl)-1,3-dioxoisoindolin-4-yl)amino)-3,6,9,12-tetraoxapentadecan-15-oate (137 mg, 0.237 mmol) was dissolved in 5 ml DCM and TFA (5 mL) was added to the reaction mixture and it was stirred for 1 hour. The mixture was concentrated with a rotary evaporator and the residue was purified by using a porapack column, the solvent was evaporated to afford the title compound (74 mg, 60% yield). $^1$H NMR (500 MHz, CHLOROFORM-d) δ 8.75-8.90 (m, 1H), 7.43 (t, J=7.86 Hz, 1H), 7.04 (d, J=6.97 Hz, 1H), 6.85 (d, J=8.56 Hz, 1H), 6.40-6.53 (m, 1H), 4.83-4.88 (m, 1H), 3.69 (td, J=5.65, 13.51 Hz, 4H), 3.55-3.64 (m, 12H), 3.41 (br. s., 2H), 2.76-2.87 (m, 1H), 2.62-2.76 (m, 3H), 2.52 (t, J=5.87 Hz, 2H), 2.02-2.11 (m, 1H) LCMS (ES$^+$): m/z 522.45 [M+1]$^+$.

Step 5: N-(3-(5-((1-(1-((2-(2,6-dioxopiperidin-3-yl)-1,3-dioxoisoindolin-4-yl)amino)-3,6,9,12-tetraoxapentadecan-15-oyl)piperidin-4-yl)(methyl)amino)-3-(pyrimidin-5-yl)-1H-pyrrolo[3,2-b]pyridin-1-yl)-2,4-difluorophenyl)propane-1-sulfonamide during 10 min, then N,N-diisopropylethylamine (39.3 mg, 0.304 mmol) was added and the mixture was stirred another 10 min. N-(2,4-difluoro-3-(5-(methyl(piperidin-4-yl)amino)-3-(pyrimidin-5-yl)-1H-pyrrolo[3,2-b]pyridin-1-yl)phenyl)propane-1-sulfonamide trifluoroacetic acid salt (67 mg, 0.101 mmol, synthesized using the synthetic procedures described in WO2012104388A1) in 1 mL of DMF was added to the reaction mixture at RT. The reaction mixture was stirred overnight. Water (1 mL) was added to the reaction mixture and extracted with EtOAc. The organic extract was evaporated with Celite® and purified with RP-MPLC. (Water-ACN (40%). Fractions with pure compound were collected and evaporated on a V10 apparatus to obtain the title compound (16 mg, 38% yield). $^1$H NMR (500 MHz, DMSO-d$_6$) δ=11.02 (s, 1H), 9.59 (s, 2H), 8.95 (s, 1H), 8.33 (s, 1H), 7.57-7.43 (m, 2H), 7.37 (br d, J=9.3 Hz, 1H), 7.23 (br s, 1H), 7.06 (d, J=8.6 Hz, 1H), 6.96 (d, J=7.0 Hz, 1H), 6.74 (d, J=9.3 Hz, 1H), 6.53 (br t, J=5.6 Hz, 1H), 4.98 (dd, J=5.5, 12.7 Hz, 1H), 4.53 (br d, J=11.4 Hz, 2H), 3.99 (br

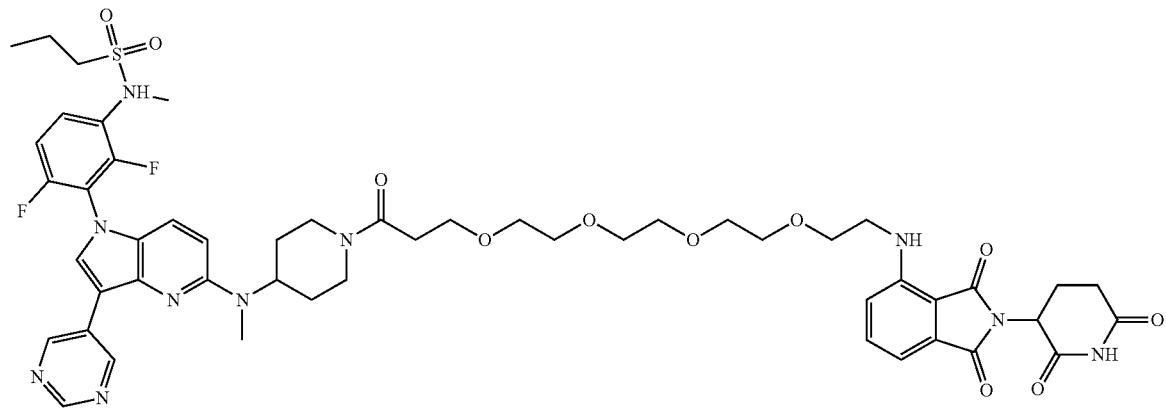 [SMILES: CCCS(=O)(=O)N(C)c1ccc(F)c(-n2cc(-c3cncnc3)c3nc(N(C)C4CCN(C(=O)CCOCCOCCOCCOCCNc5cccc6c5C(=O)N(C5CCC(=O)NC5=O)C6=O)CC4)ccc32)c1F]

1-((2-(2,6-Dioxopiperidin-3-yl)-1,3-dioxoisoindolin-4-yl)amino)-3,6,9,12-tetraoxapentadecan-15-oic acid (52 mg, 0.101 mmol) was dissolved in 0.5 mL DMF, HATU (46.3 mg, 0.122 mmol) was added at RT. The mixture was stirring d, J=12.7 Hz, 1H), 3.59-3.52 (m, 4H), 3.49-3.28 (m, 19H), 3.24-3.17 (m, 3H), 3.07 (br t, J=11.1 Hz, 2H), 2.95 (br s, 2H), 2.02-1.92 (m, 1H), 1.73-1.61 (m, 5H), 1.59-1.40 (m, 1H), 0.96-0.87 (m, 3H). LCMS (ES$^+$): m/z 1045.72 [M+1]$^+$.

Example 2

N-(3-(5-((1-(3-(2-(2-(2-((2-(2,6-dioxopiperidin-3-yl)-1,3-dioxoisoindolin-4-yl)amino)ethoxy)ethoxy)ethoxy)propanoyl)piperidin-4-yl)(methyl)amino)-3-(pyrimidin-5-yl)-1H-pyrrolo[3,2-b]pyridin-1-yl)-2,4-difluorophenyl)propane-1-sulfonamide (I-2)

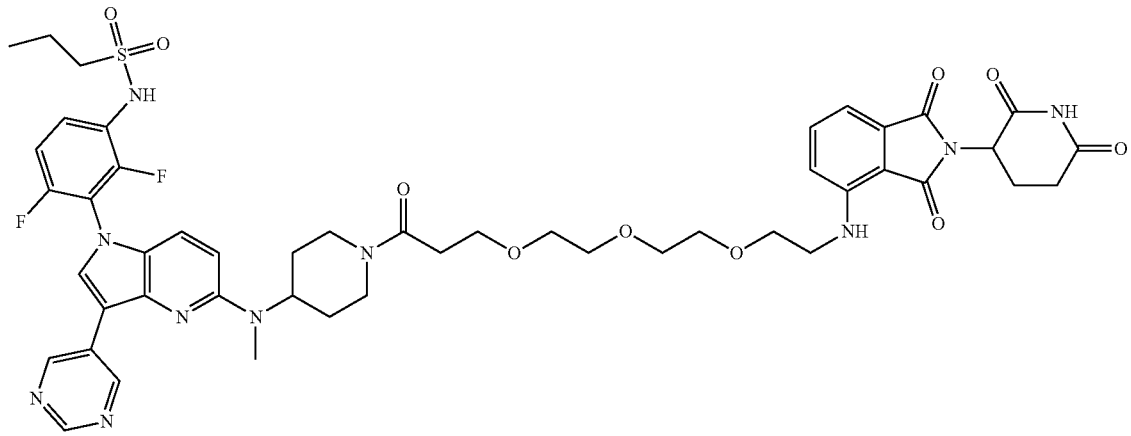 [SMILES: CCCS(=O)(=O)Nc1ccc(F)c(-n2cc(-c3cncnc3)c3nc(N(C)C4CCN(C(=O)CCOCCOCCOCCNc5cccc6c5C(=O)N(C5CCC(=O)NC5=O)C6=O)CC4)ccc32)c1F]

Step 1: Tert-butyl 3-(2-(2-(2-((2-(2,6-dioxopiperidin-3-yl)-1,3-dioxoisoindolin-4-yl)amino)ethoxy)ethoxy)ethoxy)propanoate

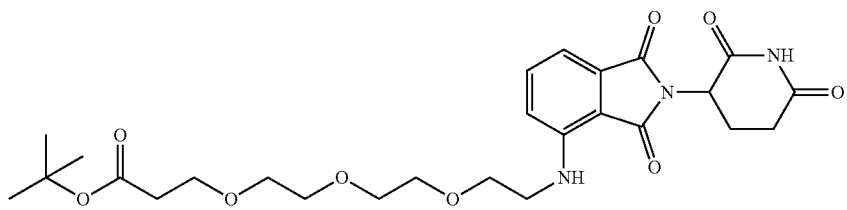 [SMILES: CC(C)(C)OC(=O)CCOCCOCCOCCNc1cccc2c1C(=O)N(C1CCC(=O)NC1=O)C2=O]

The title compound was prepared according a procedure similar to Example 1, Step 1, from tert-butyl 3-(2-(2-(2-aminoethoxy)ethoxy)ethoxy)propanoate and 2-(2,6-dioxopiperidin-3-yl)-4-fluoroisoindoline-1,3-dione to give the product (295 mg, 51% yield). $^1$H NMR (500 MHz, CDCl$_3$) δ=8.15 (br s, 1H), 7.52 (t, J=7.8 Hz, 1H), 7.13 (d, J=7.0 Hz, 1H), 6.95 (d, J=8.4 Hz, 1H), 6.51 (br s, 1H), 4.94 (dd, J=5.3, 12.3 Hz, 1H), 3.77-3.62 (m, 13H), 3.50 (q, J=5.4 Hz, 2H), 2.94-2.72 (m, 3H), 2.53 (t, J=6.5 Hz, 2H), 2.19-2.12 (m, 1H), 1.47 (s, 10H) LCMS (ES$^+$): m/z 534.37 [M+1]$^+$.

Step 2: 3-(2-(2-(2-((2-(2,6-Dioxopiperidin-3-yl)-1,3-dioxoisoindolin-4-yl)amino)ethoxy)-ethoxy)ethoxy)propanoic acid

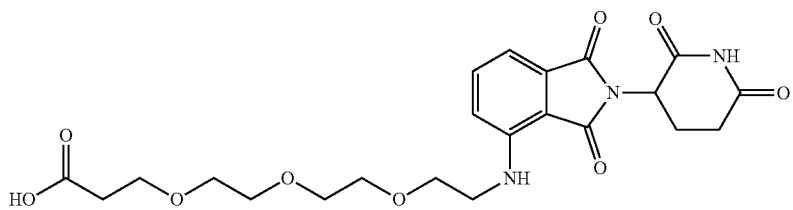 [SMILES: O=C(O)CCOCCOCCOCCNc1cccc2c1C(=O)N(C1CCC(=O)NC1=O)C2=O]

The title compound was prepared from tert-butyl 3-(2-(2-(2-((2-(2,6-dioxopiperidin-3-yl)-1,3-dioxoisoindolin-4-yl)amino)ethoxy)-ethoxy)ethoxy)propanoate in a manner similar to Example 1, step 2 to give the product (341 mg, 66%). ¹H NMR (500 MHz, CDCl₃) δ 8.61 (br. s., 1H), 7.43 (t, J=7.78 Hz, 1H), 7.04 (d, J=6.97 Hz, 1H), 6.85 (d, J=8.56 Hz, 1H), 6.46 (br. s., 1H), 4.83-4.89 (m, 1H), 3.57-3.73 (m, 15H), 3.54 (t, J=4.28 Hz, 1H), 3.40 (br. s., 2H), 2.76-2.95 (m, 1H), 2.62-2.75 (m, 3H), 2.50-2.60 (m, 2H), 2.01-2.20 (m, 1H). LCMS (ES⁺): m/z 478.45 [M+1]⁺.

Step 3: N-(3-(5-((1-(3-(2-(2-(2-((2-(2,6-dioxopiperidin-3-yl)-1,3-dioxoisoindolin-4-yl)amino)ethoxy)ethoxy)ethoxy)propanoyl)piperidin-4-yl)(methyl)amino)-3-(pyrimidin-5-yl)-1H-pyrrolo[3,2-b]pyridin-1-yl)-2,4-difluorophenyl)propane-1-sulfonamide (I-3)

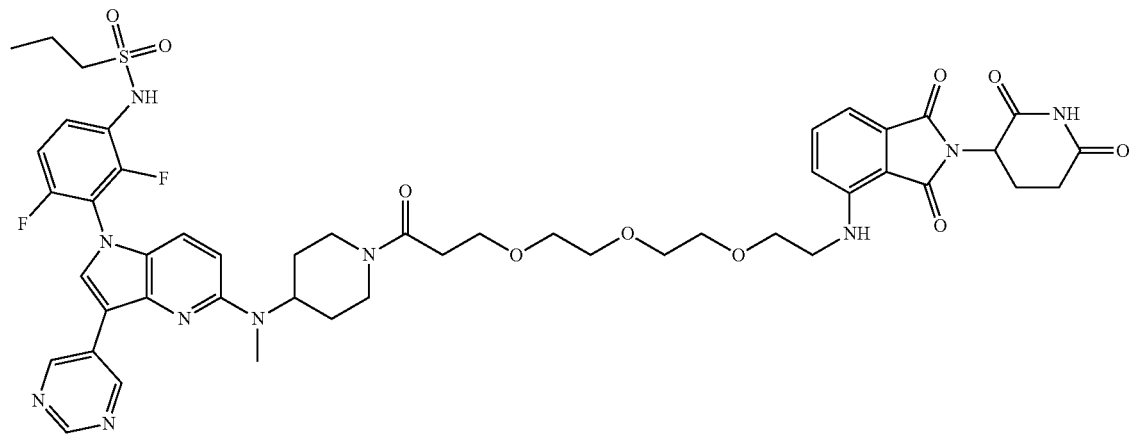 [SMILES: CCCS(=O)(=O)Nc1ccc(F)c(-n2cc(-c3cncnc3)c3nc(N(C)C4CCN(C(=O)CCOCCOCCOCCNc5cccc6c5C(=O)N(C5CCC(=O)NC5=O)C6=O)CC4)ccc32)c1F]

A procedure similar to Example 1, Step 5 using 3-(2-(2-(2-((2-(2,6-dioxopiperidin-3-yl)-1,3-dioxoisoindolin-4-yl)amino)ethoxy)-ethoxy)ethoxy)-propanoic acid (14.42 mg, 0.03 mmol) and N-(2,4-difluoro-3-(5-(methyl(piperidin-4-yl)amino)-3-(pyrimidin-5-yl)-1H-pyrrolo[3,2-b]pyridin-1-yl)phenyl)propane-1-sulfonamide trifluoroacetic acid salt (18 mg, 0.027 mmol) gave the title compound (6.87 mg, 25% yield) as a yellow powder. ¹H NMR (DMSO-d₆, 500 MHz) δ 11.0-11.3 (m, 1H), 9.9-10.1 (m, 1H), 9.77 (s, 2H), 9.14 (s, 1H), 8.52 (s, 1H), 7.6-7.8 (m, 2H), 7.5-7.6 (m, 2H), 7.2-7.3 (m, 1H), 7.1-7.2 (m, 1H), 6.9-7.0 (m, 1H), 6.7-6.8 (m, 1H), 5.0-5.3 (m, 1H), 4.7-4.8 (m, 2H), 4.1-4.2 (m, 1H), 3.6-3.8 (m, 16H), 3.2-3.3 (m, 3H), 3.0-3.1 (m, 4H), 2.4-2.5 (m, 2H), 2.1-2.2 (m, 1H), 1.8-1.9 (m, 5H), 1.6-1.7 (m, 1H), 1.11 (t, 3H, J=7.5 Hz) LCMS (ES⁺): m/z 1001.32 [M+1]⁺.

Example 3

N-(3-(5-((1-(1-((2-(2,6-dioxopiperidin-3-yl)-1,3-dioxoisoindolin-4-yl)amino)-3,6,9,12,15-pentaoxaoctadecan-18-oyl)piperidin-4-yl)(methyl)amino)-3-(pyrimidin-5-yl)-1H-pyrrolo[3,2-b]pyridin-1-yl)-2,4-difluorophenyl)propane-1-sulfonamide

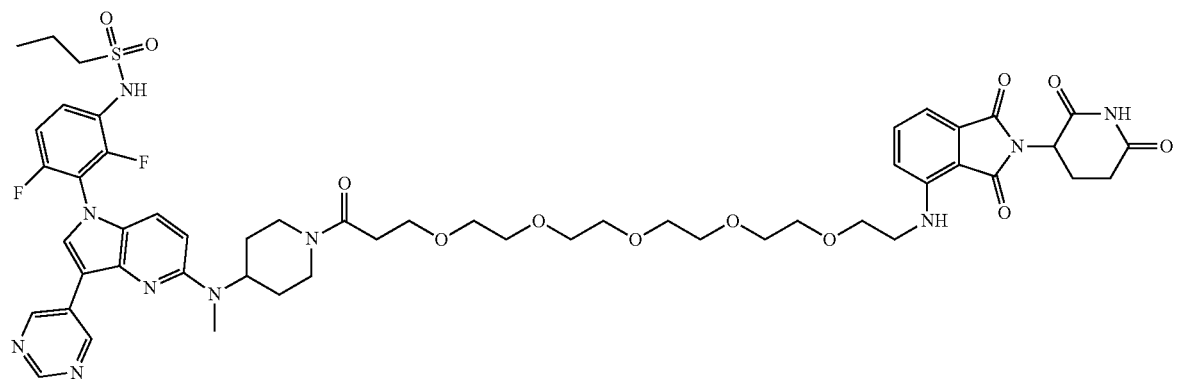 [SMILES: CCCS(=O)(=O)Nc1ccc(F)c(-n2cc(-c3cncnc3)c3nc(N(C)C4CCN(C(=O)CCOCCOCCOCCOCCOCCNc5cccc6c5C(=O)N(C5CCC(=O)NC5=O)C6=O)CC4)ccc32)c1F]

Step 1: Tert-butyl 1-((2-(2,6-dioxopiperidin-3-yl)-1,3-dioxoisoindolin-4-yl)amino)-3,6,9,12,15-pentaoxaoctadecan-18-oate

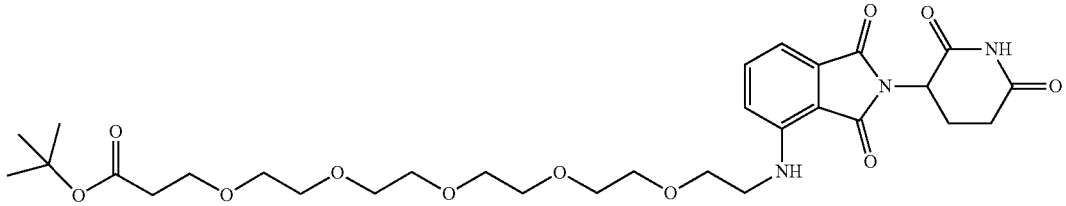 [SMILES: CC(C)(C)OC(=O)CCOCCOCCOCCOCCOCCNc1cccc2c1C(=O)N(C1CCC(=O)NC1=O)C2=O]

The title compound was prepared from tert-butyl 1-amino-3,6,9,12,15-pentaoxaoctadecan-18-oate (437 mg, 1.195 mmol) and 2-(2,6-dioxopiperidin-3-yl)-4-fluoroisoindoline-1,3-dione (300 mg, 1.086 mmol) in a manner similar to Example 1, Step 3 to give the product (472 mg, 70% yield). $^1$H NMR (500 MHz, CDCl$_3$) δ=8.22 (br s, 1H), 7.50 (t, J=7.8 Hz, 1H), 7.11 (d, J=7.1 Hz, 1H), 6.93 (d, J=8.6 Hz, 1H), 6.50 (br t, J=5.2 Hz, 1H), 4.92 (dd, J=5.3, 12.3 Hz, 1H), 3.74-3.60 (m, 19H), 3.48 (q, J=5.5 Hz, 2H), 2.92-2.70 (m, 3H), 2.50 (t, J=6.6 Hz, 2H), 2.18-2.10 (m, 1H), 1.48-1.41 (m, 9H). LCMS (ES$^+$): m/z 622.43 [M+1]$^+$.

Step 2: 1-((2-(2,6-dioxopiperidin-3-yl)-1,3-dioxoisoindolin-4-yl)amino)-3,9,12,15-pentaoxaocta-decan-18-oic acid

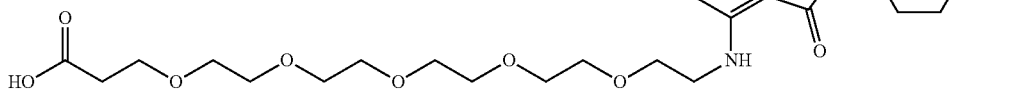

The title compound (430 mg, 98% yield) was prepared from tert-butyl 1-((2-(2,6-dioxopiperidin-3-yl)-1,3-dioxoisoindolin-4-yl)amino)-3,6,9,12,15-pentaoxaoctadecan-18-oate (472 mg, 0.760 mmol) using a procedure similar to Example 1, Step 4. $^1$H-NMR (500 MHz, CDCl$_3$) δ 8.75 (br. s., 1H), 7.43 (t, J=7.79 Hz, 1H), 7.04 (d, J=7.09 Hz, 1H), 6.85 (d, J=8.56 Hz, 1H), 4.83-4.89 (m, 1H), 3.53-3.71 (m, 20H), 3.36-3.42 (m, 2H), 2.63-2.84 (m, 3H), 2.53 (t, J=5.81 Hz, 2H), 1.94-2.11 (m, 1H). LCMS (ES$^+$): m/z 566.45 [M+1]$^+$.

Step 3: N-(3-(5-((1-(1-((2-(2,6-dioxopiperidin-3-yl)-1,3-dioxoisoindolin-4-yl)amino)-3,6,9,12,15-pentaoxaoctadecan-18-oyl)piperidin-4-yl)(methyl)amino)-3-(pyrimidin-5-yl)-1H-pyrrolo[3,2-b]pyridin-1-yl)-2,4-difluorophenyl)propane-1-sulfonamide

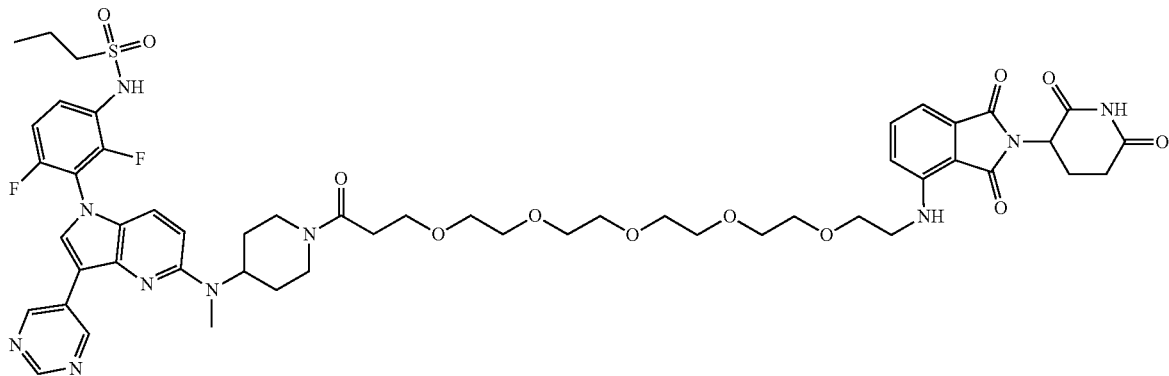 [SMILES: CCCS(=O)(=O)Nc1ccc(F)c(-n2cc(-c3cncnc3)c3nc(N(C)C4CCN(C(=O)CCOCCOCCOCCOCCOCCNc5cccc6c5C(=O)N(C5CCC(=O)NC5=O)C6=O)CC4)ccc32)c1F]

The title compound (4 mg, 14% yield) was prepared from 1-((2-(2,6-dioxopiperidin-3-yl)-1,3-dioxoisoindolin-4-yl) amino)-3,6,9,12,15-pentaoxaocta-decan-18-oic acid (15 mg, 26.5 μmol) and N-(2,4-difluoro-3-(5-(methyl(piperidin-4-yl)amino)-3-(pyrimidin-5-yl)-1H-pyrrolo[3,2-b]pyridin-1-yl)phenyl)propane-1-sulfonamide trifluoracetic acid salt (17.39 mg, 26.5 μmol) according to the procedure described in Step 5, Example 1. $^1$H NMR (500 MHz, DMSO-$d_6$) δ=11.02 (s, 1H), 9.87 (br s, 1H), 9.59 (s, 2H), 8.96 (s, 1H), 8.34 (s, 1H), 7.57-7.47 (m, 2H), 7.44-7.32 (m, 2H), 7.06 (d, J=8.6 Hz, 1H), 6.96 (d, J=7.1 Hz, 1H), 6.74 (d, J=9.3 Hz, 1H), 6.52 (br t, J=5.6 Hz, 1H), 4.98 (dd, J=5.4, 12.8 Hz, 1H), 4.53 (br d, J=11.5 Hz, 2H), 4.00 (br d, J=13.1 Hz, 1H), 3.60-3.52 (m, 4H), 3.49-3.33 (m, 19H), 3.13-3.02 (m, 3H), 2.89-2.75 (m, 4H), 1.98-1.92 (m, 1H), 1.74-1.62 (m, 5H), 1.60-1.46 (m, 1H), 0.92 (t, J=7.4 Hz, 3H). LCMS (ES$^+$): m/z 1089.89 [M+1]$^+$.

Example 4

N-(3-(5-(((1-(1-((2-(2,6-dioxopiperidin-3-yl)-1,3-dioxoisoindolin-4-yl)amino)-3,6,9,12,15,18-hexaoxaheneicosan-21-oyl)piperidin-4-yl)(methyl)amino)-3-(pyrimidin-5-yl)-1H-pyrrolo[3,2-b]pyridin-1-yl)-2,4-difluorophenyl)propane-1-sulfonamide (I-4)

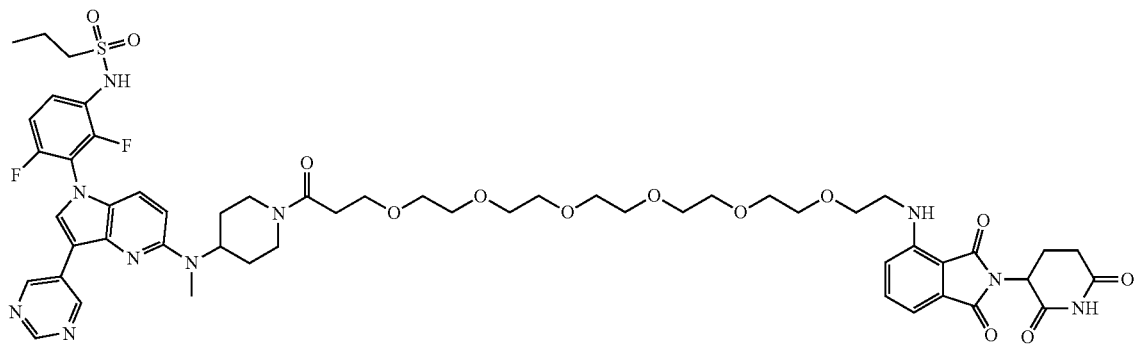 [SMILES: CCCS(=O)(=O)Nc1ccc(F)c(-n2cc(-c3cncnc3)c3nc(N(C)C4CCN(C(=O)CCOCCOCCOCCOCCOCCOCCNc5cccc6c5C(=O)N(C5CCC(=O)NC5=O)C6=O)CC4)ccc32)c1F]

Step 1: Tert-butyl 1-((2-(2,6-dioxopiperidin-3-yl)-1,3-dioxoisoindolin-4-yl)amino)-3,6,9,12,15,18-hexaoxaheneicosan-21-oate

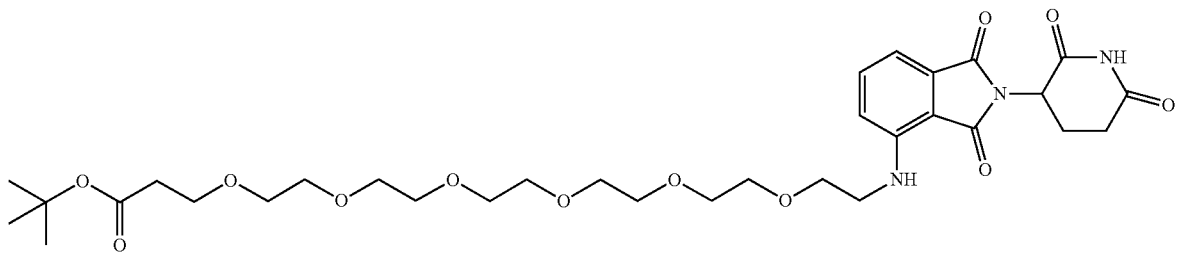 [SMILES: CC(C)(C)OC(=O)CCOCCOCCOCCOCCOCCOCCNc1cccc2c1C(=O)N(C1CCC(=O)NC1=O)C2=O]

A procedure similar to Example 1, Step 3 using tert-butyl 1-amino-3,6,9,12,15,18-hexaoxaheneicosan-21-oate (98 mg, 0.239 mmol) and 2-(2,6-dioxopiperidin-3-yl)-4-fluoroisoindoline-1,3-dione (60 mg, 0.217 mmol) to give the product (100 mg, 69% yield). $^1$H NMR (500 MHz, CDCl$_3$) δ=8.22 (br s, 1H), 7.50 (t, J=7.8 Hz, 1H), 7.11 (d, J=7.1 Hz, 1H), 6.93 (d, J=8.6 Hz, 1H), 6.50 (br t, J=5.2 Hz, 1H), 4.92 (dd, J=5.3, 12.3 Hz, 1H), 3.74-3.60 (m, 26H), 3.48 (q, J=5.5 Hz, 2H), 2.92-2.70 (m, 3H), 2.50 (t, J=6.6 Hz, 2H), 2.18-2.10 (m, 1H), 1.48-1.41 (m, 9H). LCMS (ES$^+$): m/z 666.3 [M+1]$^+$.

Step 2: 1-((2-(2,6-Dioxopiperidin-3-yl)-1,3-dioxoisoindolin-4-yl)amino)-3, 6, 9,12,15,18-hexaoxa-heneicosan-21-oic acid

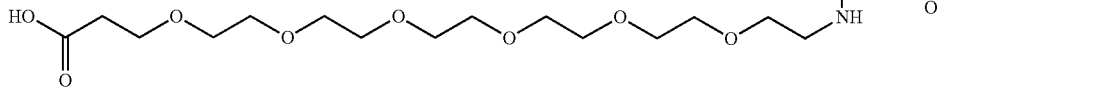

A procedure similar to Example 1, Step 4 using 1-((2-(2,6-dioxopiperidin-3-yl)-1,3-dioxoisoindolin-4-yl)amino)-3,6,9,12,15,18-hexaoxa-heneicosan-21-oic acid (100 mg, 0.150 mmol) afforded the title compound (82 mg, 90% yield). $^1$H NMR (500 MHz, CDCl$_3$) δ 8.75 (br. s., 1H), 7.43 (t, J=7.79 Hz, 1H), 7.04 (d, J=7.09 Hz, 1H), 6.85 (d, J=8.56 Hz, 1H), 4.83-4.89 (m, 1H), 3.53-3.71 (m, 24H), 3.36-3.42 (m, 2H), 2.63-2.84 (m, 3H), 2.53 (t, J=5.81 Hz, 2H), 1.94-2.11 (m, 1H). LCMS (ES$^+$): m/z 610.5 [M+1]$^+$.

Step 3: N-(3-(5-((1-(1-((2-(2,6-dioxopiperidin-3-yl)-1,3-dioxoisoindolin-4-yl)amino)-3,6,9,12,15,18-hexaoxaheneicosan-21-oyl)piperidin-4-yl)(methyl)amino)-3-(pyrimidin-5-yl)-1H-pyrrolo[3,2-b]pyridin-1-yl)-2,4-difluorophenyl)propane-1-sulfonamide

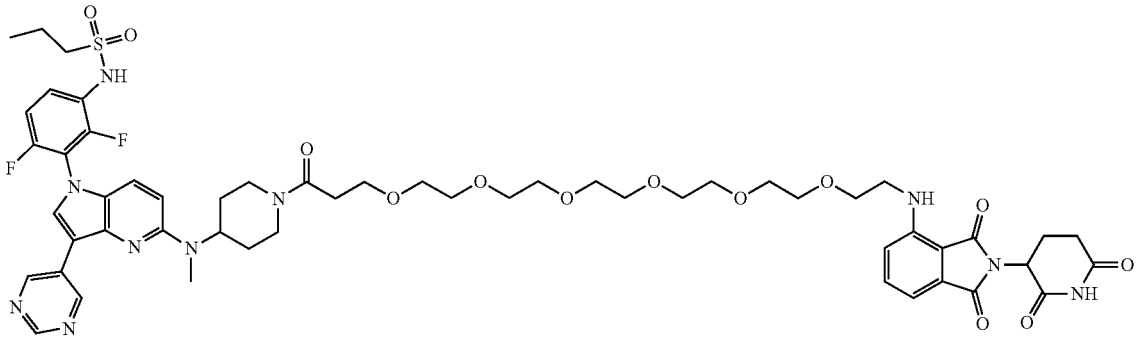 [SMILES: CCCS(=O)(=O)Nc1ccc(F)c(-n2cc(-c3cncnc3)c3nc(N(C)C4CCN(C(=O)CCOCCOCCOCCOCCOCCOCCNc5cccc6c5C(=O)N(C5CCC(=O)NC5=O)C6=O)CC4)ccc32)c1F]

A procedure similar to Example 1, Step 5 using was using 1-((2-(2,6-dioxopiperidin-3-yl)-1,3-dioxoisoindolin-4-yl)amino)-3,6,9,12,15,18-hexaoxa-heneicosan-21-oic acid (9.15 mg, 0.015 mmol) and N-(2,4-difluoro-3-(5-(methyl(piperidin-4-yl)amino)-3-(pyrimidin-5-yl)-1H-pyrrolo[3,2-b]pyridin-1-yl)phenyl)propane-1-sulfonamide trifluoroacetic acid salt (8.2 mg, 0.013 mmol) afforded the title compound as a yellow powder (2 mg, 14% yield). $^1$H NMR (DMSO-$d_6$, 500 MHz) δ 10.9-11.2 (m, 1H), 9.66 (s, 2H), 9.03 (s, 1H), 8.41 (s, 1H), 7.5-7.6 (m, 2H), 7.46 (d, 1H, J=9.3 Hz), 7.3-7.4 (m, 1H), 7.14 (d, 1H, J=8.6 Hz), 7.0-7.1 (m, 1H), 6.82 (d, 1H, J=9.3 Hz), 6.6-6.6 (m, 1H), 5.0-5.1 (m, 1H), 4.6-4.7 (m, 2H), 4.0-4.1 (m, 1H), 3.6-3.7 (m, 4H), 3.4-3.6 (m, 25H), 3.0-3.2 (m, 3H), 2.8-3.0 (m, 4H), 2.4-2.5 (m, 2H), 2.0-2.1 (m, 1H), 1.7-1.8 (m, 5H), 1.5-1.6 (m, 1H), 0.99 (t, 3H, J=7.5 Hz) LCMS (ES$^+$): m/z 1133.46 [M+1]$^+$.

Example 5

N-(3-(5-((1-(1-((2-(2,6-dioxopiperidin-3-yl)-1,3-dioxoisoindolin-4-yl)amino)-3,6,9,12,15,18,21,24-octaoxaheptacosan-27-oyl)piperidin-4-yl)(methyl)amino)-3-(pyrimidin-5-yl)-1H-pyrrolo[3,2-b]pyridin-1-yl)-2,4-difluorophenyl)propane-1-sulfonamide (I-5)

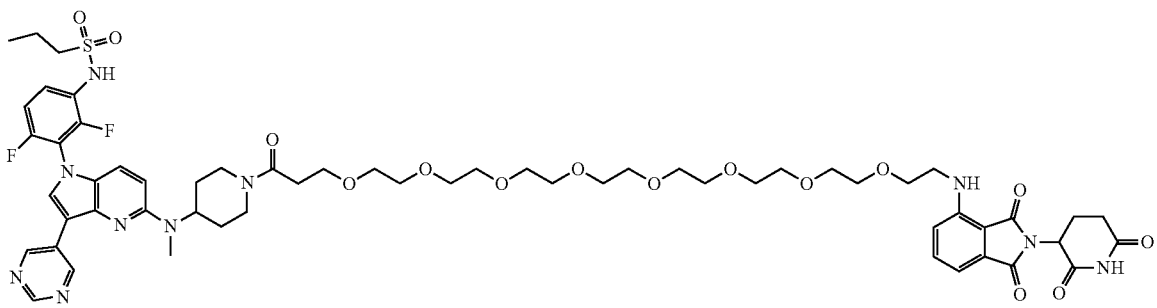 [SMILES: CCCS(=O)(=O)Nc1ccc(F)c(-n2cc(-c3cncnc3)c3nc(N(C)C4CCN(C(=O)CCOCCOCCOCCOCCOCCOCCOCCOCCNc5cccc6c5C(=O)N(C5CCC(=O)NC5=O)C6=O)CC4)ccc32)c1F]

Step 1: tert-butyl 1-((2-(2,6-dioxopiperidin-3-yl)-1,3-dioxoisoindolin-4-yl)amino)-3,6,9,12,15,18,21,24-octaoxaheptacosan-27-oate

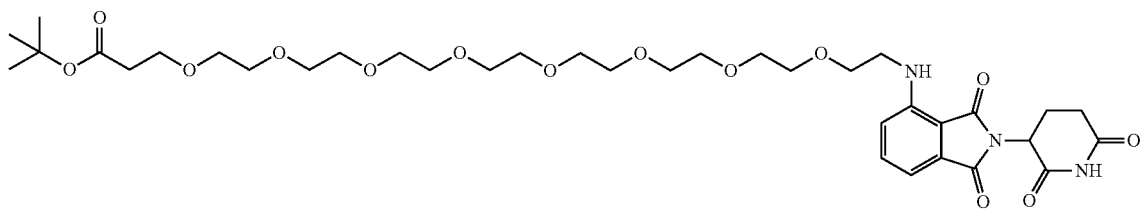 [SMILES: CC(C)(C)OC(=O)CCOCCOCCOCCOCCOCCOCCOCCOCCNc1cccc2c1C(=O)N(C1CCC(=O)NC1=O)C2=O]

The procedure followed was similar to Example 1, step 1, using tert-butyl 1-amino-3,6,9,12,15,18,21,24-octaoxaheptacosan-27-oate (59.5 mg, 0.119 mmol) and 2-(2,6-dioxopiperidin-3-yl)-4-fluoroisoindoline-1,3-dione (30 mg, 0.109 mmol) to give the product (40 mg, 49% yield). $^1$H NMR (500 MHz, CDCl$_3$) δ=8.22 (br s, 1H), 7.50 (t, J=7.8 Hz, 1H), 7.11 (d, J=7.1 Hz, 1H), 6.93 (d, J=8.6 Hz, 1H), 6.50 (br t, J=5.2 Hz, 1H), 4.92 (dd, J=5.3, 12.3 Hz, 1H), 3.74-3.60 (m, 32H), 3.48 (q, J=5.5 Hz, 2H), 2.92-2.70 (m, 3H), 2.50 (t, J=6.6Hz, 2H), 2.18-2.10 (m, 1H), 1.48-1.41 (m, 9H). LCMS (ES$^+$): m/z 754.52 [M+1]$^+$.

Step 2: 1-((2-(2,6-dioxopiperidin-3-yl)-1,3-dioxoisoindolin-4-yl)amino)-3,6,9,12,15,18,21,24-octaoxaheptacosan-27-oic acid

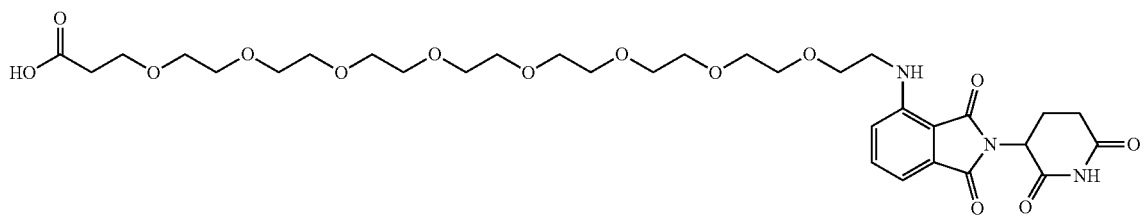 [SMILES: O=C(O)CCOCCOCCOCCOCCOCCOCCOCCOCCNc1cccc2c1C(=O)N(C1CCC(=O)NC1=O)C2=O]

The procedure used was similar to Example 1, Step 2 using tert-butyl 1-((2-(2,6-dioxopiperidin-3-yl)-1,3-dioxoisoindolin-4-yl)amino)-3,6,9,12,15,18,21,24-octaoxaheptacosan-27-oate (40 mg, 0.053 mmol) to afford the title compound (33 mg, 90% yield). $^1$H NMR (500 MHz, CDCl$_3$) δ 8.75 (br. s., 1H), 7.43 (t, J=7.79 Hz, 1H), 7.04 (d, J=7.09 Hz, 1H), 6.85 (d, J=8.56 Hz, 1H), 4.83-4.89 (m, 1H), 3.53-3.71 (m, 32H), 3.36-3.42 (m, 2H), 2.63-2.84 (m, 3H), 2.53 (t, J=5.81 Hz, 2H), 1.94-2.11 (m, 1H). LCMS (ES$^+$): m/z 698.39 [M+1]$^+$.

Step 3: N-(3-(5-((1-(1-((2-(2,6-dioxopiperidin-3-yl)-1,3-dioxoisoindolin-4-yl)amino)-3,6,9,12,15,18,21,24-octaoxaheptacosan-27-oyl)piperidin-4-yl)(methyl)amino)-3-(pyrimidin-5-yl)-1H-pyrrolo[3,2-b]pyridin-1-yl)-2,4-difluorophenyl)propane-1-sulfonamide

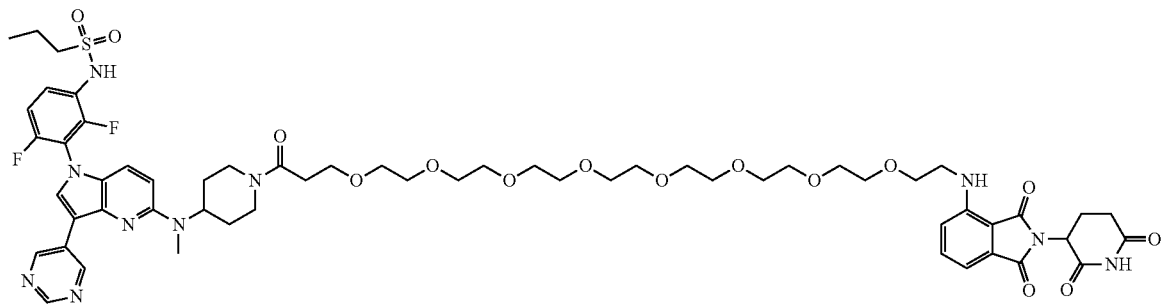 [SMILES: CCCS(=O)(=O)Nc1ccc(F)c(-n2cc(-c3cncnc3)c3nc(N(C)C4CCN(C(=O)CCOCCOCCOCCOCCOCCOCCOCCOCCNc5cccc6c5C(=O)N(C5CCC(=O)NC5=O)C6=O)CC4)ccc32)c1F]

A procedure similar to Example 1, Step 5 using 1-((2-(2,6-dioxopiperidin-3-yl)-1,3-dioxoisoindolin-4-yl)amino)-3,6,9,12,15,18,21,24-octaoxaheptacosan-27-oic acid (17.64 mg, 0.027 mmol) and N-(2,4-difluoro-3-(5-(methyl(piperidin-4-yl)amino)-3-(pyrimidin-5-yl)-1H-pyrrolo[3,2-b]pyridin-1-yl)phenyl)propane-1-sulfonamide trifluoroacetic acid salt (13.84 mg, 0.021 mmol) afforded the title compound as a yellow powder (2.7 mg, 10% yield). $^1$H NMR (DMSO-d6, 500 MHz) δ 11.1-11.1 (m, 1H), 9.8-10.0 (m, 1H), 9.66 (s, 2H), 9.04 (s, 1H), 8.42 (s, 1H), 7.5-7.6 (m, 2H), 7.4-7.5 (m, 2H), 7.14 (d, 1H, J=8.6 Hz), 7.04 (d, 1H, J=7.0 Hz), 6.82 (d, 1H, J=9.3 Hz), 6.60 (br. t., 1H, J=5.7 Hz), 5.0-5.1 (m, 1H), 4.5-4.7 (m, 2H), 4.0-4.1 (m, 1H), 3.6-3.7 (m, 4H), 3.4-3.6 (m, 35H), 3.1-3.2 (m, 3H), 2.8-3.0 (m, 4H), 2.4-2.5 (m, 2H), 2.0-2.1 (m,1H), 1.7-1.8 (m, 5H), 1.5-1.7 (m, 1H), 1.00 (t, 3H, J=7.5 Hz) LCMS (ES$^+$): m/z 1221.57 [M+1]$^+$.

Example 6

4-(4-((1-(2,6-Difluoro-3-(propylsulfonamido)phenyl)-3-(pyrimidin-5-yl)-1H-pyrrolo[3,2-b]pyridin-5-yl)(methyl)amino)piperidin-1-yl)-N-(3-(2-(2-(3-((2-(2,6-dioxopiperidin-3-yl)-1,3-dioxoisoindolin-4-yl)amino)propoxy)ethoxy)ethoxy)propyl)-4-oxobutanamide (I-6)

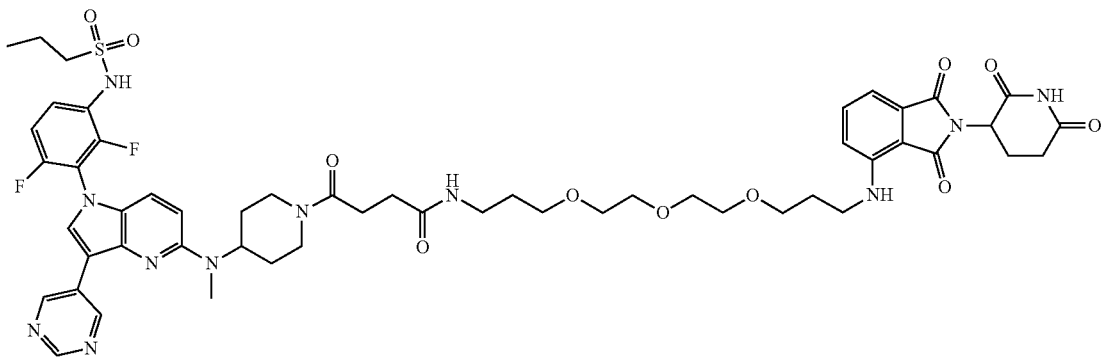 [SMILES: CCCS(=O)(=O)Nc1ccc(F)c(-n2cc(-c3cncnc3)c3nc(N(C)C4CCN(C(=O)CCC(=O)NCCCOCCOCCOCCCNc5cccc6c5C(=O)N(C5CCC(=O)NC5=O)C6=O)CC4)ccc32)c1F]

Step 1: 4-((3-(2-(2-(3-Aminopropoxy)ethoxy)ethoxy)propyl)amino)-2-(2,6-dioxopiperidin-3-yl)isoindoline-1,3-dione trifluoroacetic acid salt

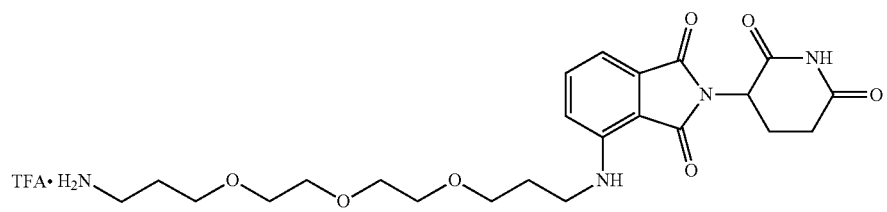 [SMILES: NCCCOCCOCCOCCCNc1cccc2c1C(=O)N(C1CCC(=O)NC1=O)C2=O ; "TFA·"]

A mixture of N-Boc-4,7,10-trioxa-1,13-tridecanediamine (232 mg, 0.724 mmol), 2-(2,6-dioxopiperidin-3-yl)-4-fluoroisoindoline-1,3-dione (200 mg, 0.724 mmol) and N,N-diisopropylethylamine (281 mg, 2.172 mmol) in 1,4-dioxane (3 ml) was stirred at 90° C. overnight. After addition of Celite®, the reaction mixture was concentrated with a rotary evaporator and purified with normal phase chromatography to obtain 210 mg of desired Boc compound compound, which was deprotected in 1 ml of trifluoroacetic acid (826 mg, 7.24 mmol) in 1 ml of DCM. 200 mg of (0.322 mmol, 44.4% yield) was synthesized. LCMS (ES$^+$): m/z 477.26 [M+1]$^+$.

Step 2: tert-butyl 1-((2-(2,6-dioxopiperidin-3-yl)-1,3-dioxoisoindolin-4-yl)amino)-15-oxo-4,7,10-trioxa-14-azaoctadecan-18-oate

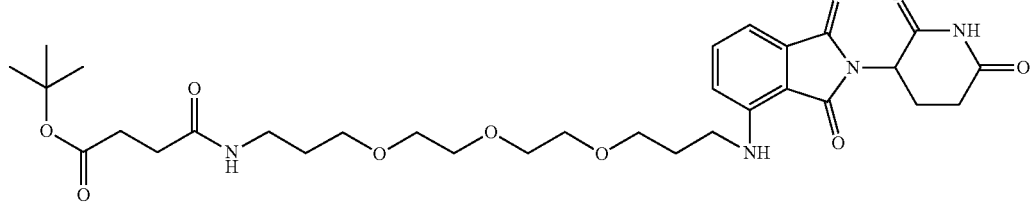

A portion of t-butyl hydrogen succinate (21.93 mg, 0.126 mmol) was dissolved in N,N-dimethylformamide (DMF) (2 ml), then HATU (52.2 mg, 0.137 mmol) was added at RT. The mixture was stirring during 10 min and N,N-dimethylformamide (DMF) (2 mL) was added and the mixture was stirred for another 10 min. 4-((3-(2-(2-(3-aminopropoxy)ethoxy)ethoxy)propyl)amino)-2-(2,6-dioxopiperidin-3-yl) isoindoline-1,3-dione trifluoroacetic acid salt (67.6 mg, 0.114 mmol) was dissolved in 1 mL of DMF. The reaction mixture was stirred overnight at RT. The reaction mixture was evaporated with a Celite® and purified by normal phase silica gel, eluting with DCM-acetonitrile (0% to 100% of DCM). The desired fractions were collected, concentrated and dried on the rotavap to afford 58 mg of the desired compound. Yield 80%. $^1$H NMR (500 MHz, DMSO-d$_6$) δ=11.09 (s, 1H), 7.78 (br s, 1H), 7.59 (br t, J=7.7 Hz, 1H), 7.11 (br d, J=8.6 Hz, 1H), 7.03 (br d, J=7.0 Hz, 1H), 6.68 (br s, 1H), 5.05 (br dd, J=5.1, 12.6 Hz, 1H), 3.56 (br s, 2H), 3.54-3.45 (m, 8H), 3.41-3.35 (m, 4H), 3.06 (q, J=6.3 Hz, 2H), 2.94-2.85 (m, 1H), 2.64-2.53 (m, 2H), 2.38 (br t, J=6.7 Hz, 2H), 2.27 (br t, J=6.8 Hz, 2H), 2.06-2.00 (m, 1H), 1.82 (br t, J=6.1 Hz, 2H), 1.60 (quin, J=6.4 Hz, 2H), 1.37 (s, 9H). LCMS (ES$^+$): m/z 633.6 [M+1]$^+$.

Step 3: 1-((2-(2,6-Dioxopiperidin-3-yl)-1,3-dioxoisoindolin-4-yl)amino)-15-oxo-4,7,10-trioxa-14-azaoctadecan-18-oic acid

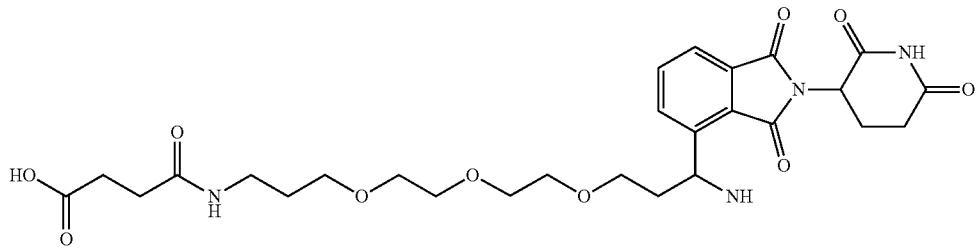 [SMILES: NC(CCOCCOCCOCCCNC(=O)CCC(=O)O)c1cccc2c1C(=O)N(C1CCC(=O)NC1=O)C2=O]

Tert-butyl 1-((2-(2,6-dioxopiperidin-3-yl)-1,3-dioxoisoindolin-4-yl)amino)-15-oxo-4,7,10-trioxa-14-azaoctadecan-18-oate (58 mg, 0.092 mmol) was dissolved in 2 mL of trifluoroacetic acid and DCM mixture (1:1). The reaction mixture was stirred overnight and evaporated using a V10 apparatus to afford the title compound with 95% yield. LCMS (ES+): m/z 577.25[M+1]+.

Step 4: 4-(4-((1-(2,6-Difluoro-3-(propylsulfonamido)phenyl)-3-(pyrimidin-5-yl)-1H-pyrrolo[3,2-b]pyridin-5-yl)(methyl)amino)piperidin-1-yl)-N-(3-(2-(2-(3-((2-(2,6-dioxopiperidin-3-yl)-1,3-dioxoisoindolin-4-yl)amino)propoxy)ethoxy)ethoxy)propyl)-4-oxobutanamide 4.59 (br d, J=11.7 Hz, 2H), 4.06 (br d, J=12.3 Hz, 1H), 3.58-3.44 (m, 12H), 3.43-3.36 (m, 2H), 3.23-3.13 (m, 2H), 3.08 (q, J=6.5 Hz, 2H), 2.98-2.85 (m, 4H), 2.68-2.62 (m, 2H), 2.61-2.56 (m, 4H), 2.47-2.30 (m, 3H), 2.08-1.92 (m, 2H), 1.85-1.70 (m, 6H), 1.68-1.52 (m, 2H), 1.00 (t, J=7.4 Hz, 3H). LCMS (ES+): m/z 1100.27 [M+1]+.

Example 7

Kinase Inhibition Assays: B-Raf (V600E) (h)

b-Raf (V599E) (h) was incubated with 25 mM Tris/HCl pH 7.5, 0.2 mM EGTA, 10 mM DTT, 0.01% Triton X-100, 0.5 mM, sodium orthovandate, 0.5 mM 6-glycerophosphate, 1% glycerol, 34 nM unactive MEK1, 69 nM unactive

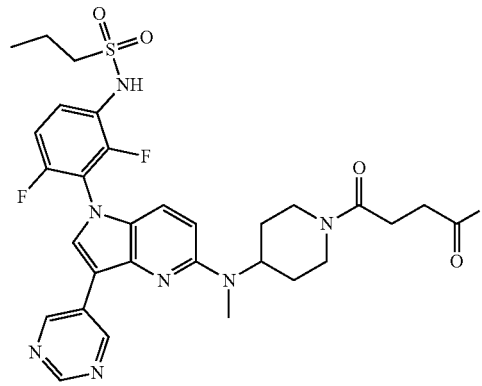
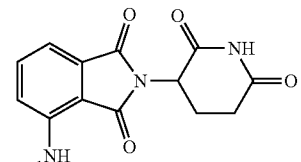

The procedure used was similar to Example 1, Step 5 using 1-((2-(2,6-dioxopiperidin-3-yl)-1,3-dioxoisoindolin-4-yl)amino)-15-oxo-4,7,10-trioxa-14-azaoctadecan-18-oic acid (12.89 mg, 0.022 mmol) and N-(2,4-difluoro-3-(5-(methyl(piperidin-4-yl)amino)-3-(pyrimidin-5-yl)-1H-pyrrolo[3,2-b]pyridin-1-yl)phenyl)propane-1-sulfonamide trifluoroacetic acid salt (13.5 mg, 0.021 mmol) to afford the title compound as a yellowish powder (18 mg, 22% yield). 1H NMR (500 MHz, DMSO-d6) δ=11.09 (s, 1H), 9.92 (br s, 1H), 9.66 (s, 2H), 9.04 (s, 1H), 8.42 (s, 1H), 7.79 (br t, J=5.4 Hz, 1H), 7.64-7.54 (m, 2H), 7.52-7.41 (m, 2H), 7.10 (d, J=8.7 Hz, 1H), 7.02 (d, J=7.1 Hz, 1H), 6.82 (d, J=9.3 Hz, 1H), 6.67 (br t, J=5.6 Hz, 1H), 5.05 (dd, J=5.4, 12.7 Hz, 1H), MAPK2, 0.5 mg/mL myelin basic protein, and 10 mM Magnesium acetate and [9-33P]-ATP (specific activity and concentration as required). The reaction was initiated by the addition of the Mg/ATP mix. After incubation for 40 minutes at room temperature, the reaction was stopped by the addition of phosphoric acid to a concentration of 0.5%. 10 μL of the reaction was then spotted onto a P30 filtermat and washed four times for 4 minutes in 0.425% phosphoric acid and once in methanol prior to drying and scintillation counting. Similar protocols were used for other kinase assays employing the kinase of interest to generate the data in Table 1.

TABLE 1

| Entry | E3 Ligase | E3 Ligase Binder | Linker | Linker Length (Å) | BRAF Binder | IC$_{50}$(nM) BRAF$^{V600E}$ | IC$_{50}$(nM) BRAF | IC$_{50}$(nM) CRAF | IC$_{50}$(nM) ARAF | DC$_{max}$(%) BRAF$^{V600E}$ | DC$_{50}$(nM) BRAF$^{V600E}$ |
|---|---|---|---|---|---|---|---|---|---|---|---|
| 1 | - | - | - | ND | Dabrafenib #1 | 13 | ND | 11 | 169 | 0 | - |
| 2 | Cereblon | Pomalidomide | PEG$_3$ | 14.6 | Dabrafenib #1 | 47 | ND | 22 | >10,000 | 0 | - |
| 3 | Cereblon | Pomalidomide | PEG$_4$ | 18.2 | Dabrafenib #1 | 25 | ND | 12 | >10,000 | ND | ND |
| 4 | Cereblon | Pomalidomide | PEG$_5$ | 21.8 | Dabrafenib #1 | 22 | ND | 10 | 3487 | ND | ND |
| 5 | Cereblon | Pomalidomide | 3C-PEG$_3$ | 20.3 | Dabrafenib #1 | 97 | 227 | 206 | 2557 | 0 | - |
| 6 | Cereblon | Pomalidomide | 3C-PEG$_4$ | 24.0 | Dabrafenib #1 | 122 | ND | 175 | 6847 | 0 | - |
| 7 | Cereblon | Pomalidomide | 3C-PEG$_5$ | 26.6 | Dabrafenib #1 | 99 | ND | 128 | 3495 | ND | ND |
| 8 | Cereblon | Pomalidomide | 3C-PEG$_6$ | 29.4 | Dabrafenib #1 | 199 | 372 | 212 | 7523 | 0 | - |
| 9 | Cereblon | Pomalidomide | PEG$_5$-PEG$_5$ | 46.1 | Dabrafenib #1 | 243 | 672 | 510 | 6723 | 0 | - |

TABLE 1-continued

| | | | | | | | | | | | |
|---|---|---|---|---|---|---|---|---|---|---|---|
| 10 | Cereblon | Thalidomide | 1C-6C | 10.2 | Dabrafenib #1 | 51 | 11.1 | 105 | 5803 | 0 | - |
| 11 | VHL | VH032 | 2C-6C | 13.4 | Dabrafenib #1 | 73 | 154 | 123 | >10,000 | 0 | - |
| 12 | VHL | VH032 | PEG$_4$ | 19.5 | Dabrafenib #2 | 58 | 136 | 201 | 3339 | 0 | - |
| 13 | Cereblon | Pomalidomide | PEG$_3$ | 14.7 | Dabrafenib #2 | 26 | 105 | 73 | 2341 | 0 | - |
| 14 | - | - | - | ND | Dabrafenib #2 | 15 | 64 | 36 | 344 | 0 | - |
| 15 | - | - | - | ND | BI 882370* | 31 | ND | 64 | 323 | 0 | - |
| 16 | Cereblon | Pomalidomide | PEG$_3$ | 15.6 | BI 882370* | 65 | ND | 532 | >10,000 | 60 | 10 |
| 17 | Cereblon | Pomalidomide | PEG$_4$ | 19.1 | BI 882370* | 12 | 58 | 167 | 2222 | 82 | 15 |
| 18 | Cereblon | Pomalidomide | PEG$_6$ | 22.7 | BI 882370* | 25 | 66 | 223 | 3619 | 73 | 50 |
| 19 | Cereblon | Pomalidomide | PEG$_6$ | 26.1 | BI 882370* | 83 | ND | 542 | 6550 | 60 | 100 |
| 20 | Cereblon | Pomalidomide | PEG$_8$ | 33.3 | BI 882370* | 85 | ND | 592 | 4907 | 40 | 75 |
| 21 | Cereblon | Pomalidomide | PEG$_3$-2C-2C | 22.9 | BI 882370* | 82 | ND | 468 | 3343 | 29 | 20 |
| 22 | VHL | VH032 | PEG$_4$ | 19.2 | BI 882370* | - | ND | - | - | 0 | - |

ND means not determined

Example 8

Cellular Degradation Assays

Cell culture and compound treatment: A375 or SK-Mel-28 cells were obtained from ATCC and cultured in Dulbecco's Modified Eagle Media (DMEM) supplemented with 10% FBS, penicillin and streptomycin, at 37° C., 5% CO$_2$. Cells grown in 6-well plates were treated for 24 hours with test compounds (solubilized in DMSO) or 0.1% DMSO vehicle control. Cells were harvested by first washing with 1× phosphate-buffered saline (PBS), then scrapping into 1 ml of PBS supplemented with 1 mM phenylmethylsulfonyl-flouride (PMSF). Cell pellets were obtained after a centrifugation at 300-350×g for 2 min, and immediately snap frozen in liquid nitrogen.

Cell lysis and Western blot analysis: Cell pellets were thawed and lysed by pipetting in lysis buffer (50 mM HEPES (pH 7.4), 150 mM NaCl, 5 mM EDTA, 0.5% NP-40, 5 mM NaF, 10% glycerol), with Roche protease inhibitor cocktail (5056489001) and phosphatase inhibitor cocktail PhosStop (4906845001) added fresh before use. The whole cell lysate was clarified by centrifugation at 15,000-20,000×g for 20 min and supernatant was collected. Total protein concentration in the clarified lysate was determination by Bradford assay (Bio-Rad), and 30-50 ug of protein was separated through SDS-PAGE, transferred onto nitrocellulose membrane and subject to standard immunoblotting protocol. Band intensities were quantified by Bio-Rad Image Lab software. Antibodies to B-Raf (sc-5284), A-Raf (sc-166771), phosphor MEK1/2, pS218/222 (sc-7995), phosphor ERK1/2 (sc-7383) were purchased from Santa Cruz; C-Raf (9422), MEK1/2 (9122), ERK1/2 (9102) from Cell Signaling; p27 (610242) from BD Biosciences. Antibody to the loading control α-tubulin was obtained from Sigma-Aldrich (6199).

Results

Figure 2:
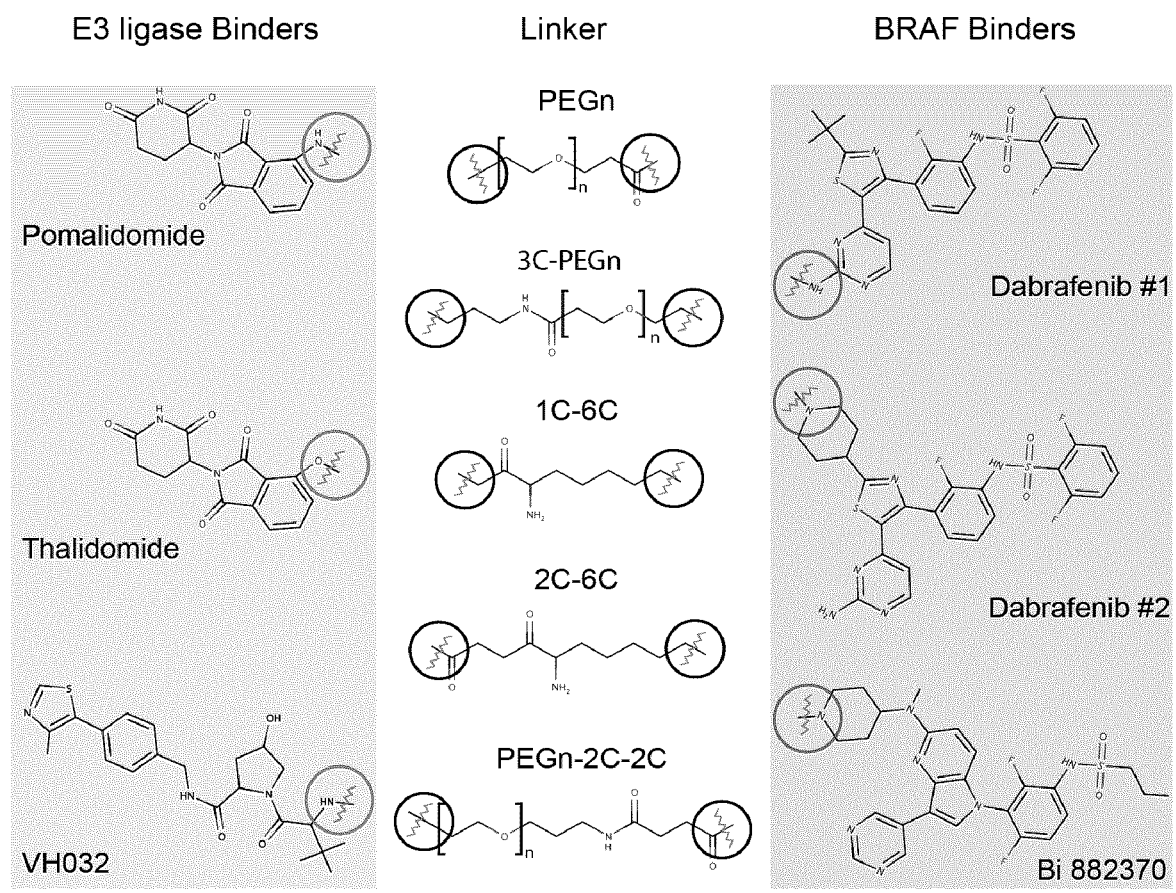
FIG. 2 shows structures of exemplary and comparative E3 ubiquitin ligase binders, linkers and B-Raf binders.

Table 1 shows the binding, inhibitory, and degradation values for the various exemplary and comparative PROTAC compounds whose structures are shown in FIG. 2.

Figure 3:
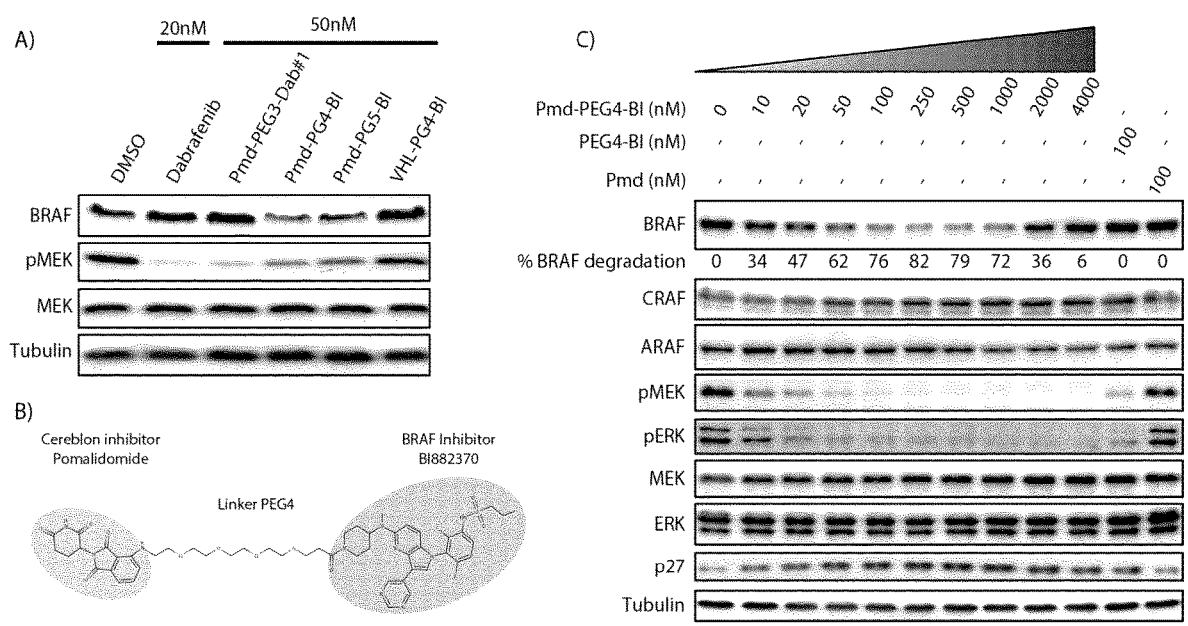
FIGS. 3A and 3C show Western blot analysis of B-Raf degradation from cells treated with exemplary compounds of the application and comparative compounds of the application.
FIG. 3B shows the structure of an exemplary compound of the application.
Figure 4:
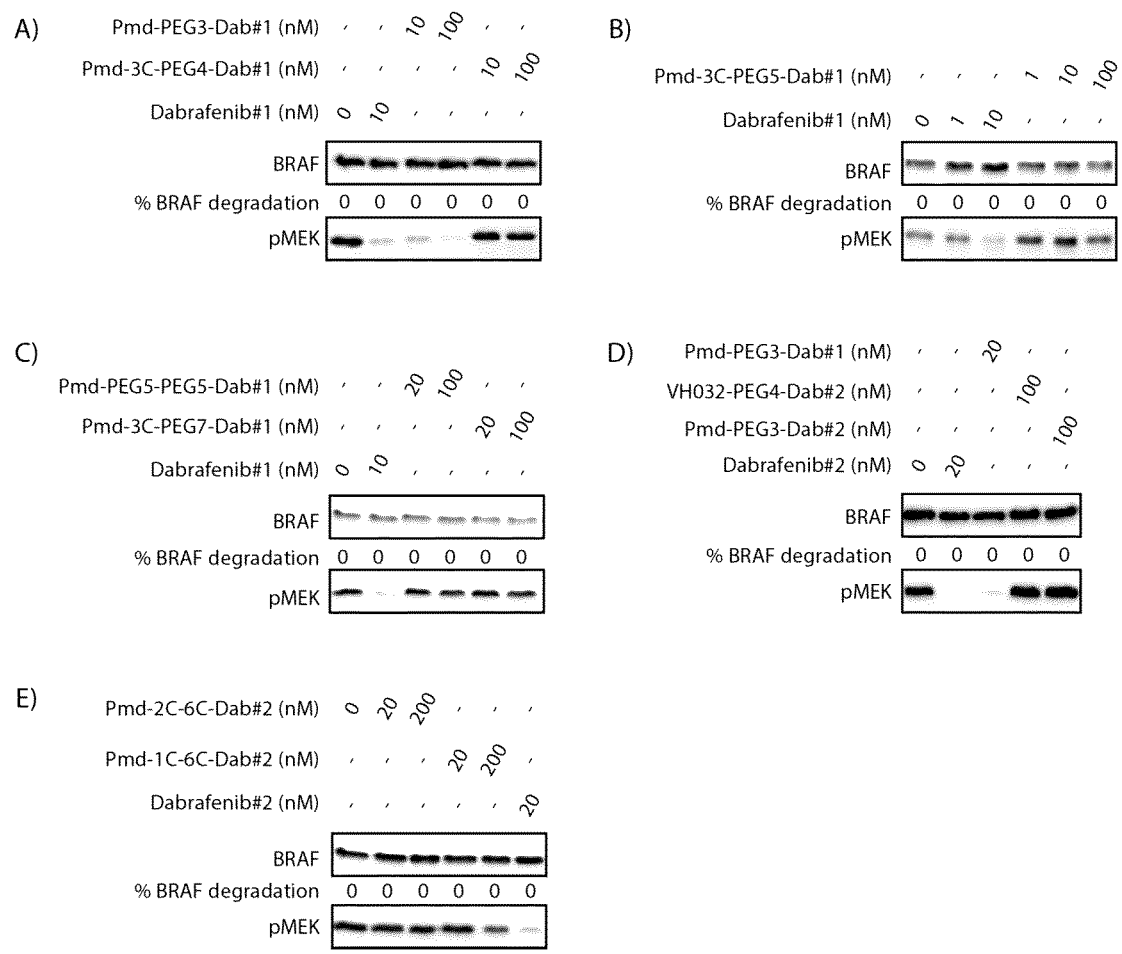
FIG. 4 shows Western blot analysis of B-Raf degradation in A375 cells treated with comparative compounds
Figure 5:
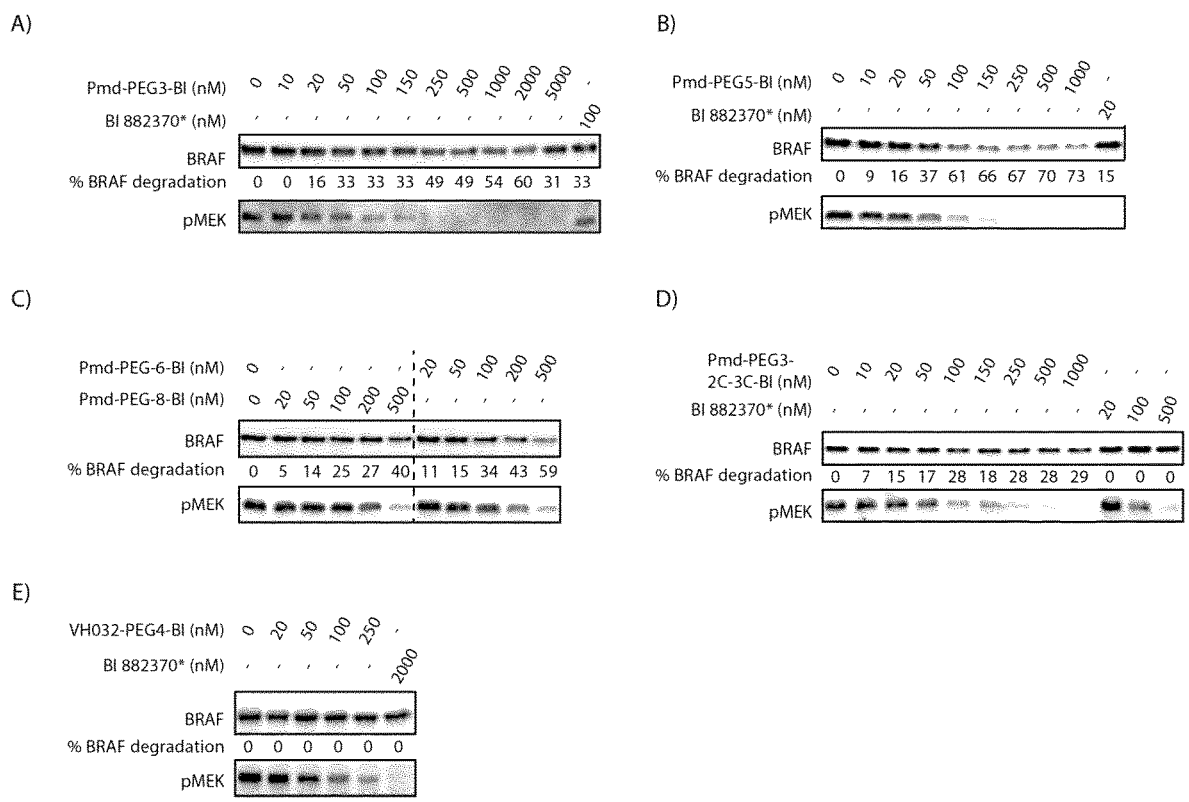
FIG. 5 shows Western blot analysis of B-Raf degradation in A375 cells treated with exemplary compounds of the application.

FIG. 3A shows an immunoblot analysis illustrating effects of selected dabrafenib- and BI-882370 (BI)-based compounds on BRAF level and MEK phosphorylation. The concentration of the parent inhibitor dabrafenib was 20 nM while the concentration of the PROTAC inhibitors was 50 nM. As determined by immunoblot, no degradation of BRAF$^{V600E}$ was observed with dabrafenib, the dabrafenib-based heterobifunctional molecules and the VH032 (VHL)-BI heterobifunctional molecules. In contrast, degradation of BRAF$^{V600E}$ was observed with the two exemplified Pomalidomide (Pmd)-BI heterobifunctional molecules. FIG. 3C shows an immunoblot analysis probing the cellular effects of Pmd-PEG$_4$-BI on ARAF, BRAF and CRAF levels and on the phosphorylation of MEK and ERK kinases in a dose-dependent manner. Pmd-PEG$_4$-BI was incubated with the A375 human melanoma cells for 24 hrs. The concentration of the negative control BI-PEG$_4$ and Pmd was 100 nM. The Pmd-PEG$_4$-BI inhibitor was tested in a concentration range from 0 to 4000 nM. Negative control BI-PEG$_4$ showed inhibition of downstream MEK and ERK kinase phosphorylation, but no degradation activity on the ARAF, BRAF and CRAF kinases. The PROTAC compound BI-PEG$_4$-Pmd showed inhibition of downstream MEK and ERK kinase phosphorylation (BRAF$^{V600E}$ IC$_{50}$=20 nM) with a selective ability to degrade BRAF$^{V600E}$ kinase (DC$_{50}$=20 nM; DC$_{max}$=80%), but not ARAF and CRAF.

FIGS. 4A-4E show immunoblot analysis demonstrating the ability of dabrafenib-based PROTACs to degrade BRAF and inhibit MEK kinase phosphorylation. Pmd-PEG$_3$-Dabrafenib#1 (FIG. 4A), Pmd-3C-PEG$_4$-Dabrafenib#1 (FIG. 4A), Pmd-3C-PEG$_5$-Dabrafenib#1 (FIG. 4B), Pmd-PEG$_5$-PEG$_5$-Dabrafenib#1 (FIG. 4C), Pmd-3C-PEG$_7$-Dabrafenib#1 (FIG. 4C), Pmd-PEG$_3$-Dabrafenib#1 ((FIG. 4D), Pmd-PEG$_3$-Dabrafenib#2 ((FIG. 4D), V032-PEG$_4$-Dabrafenib#2 (FIG. 4D), Pmd-20-6C-Dabrafenib#2 (FIG. 4E), Pmd-1C-6C-Dabrafenib#2 (FIG. 4E) and the parent compound Dabrafenib were incubated with the A375 human melanoma cells for 24 hrs. No degradation of BRAF$^{V600E}$ was observed with any of the dabrafenib-based PROTACs.

FIGS. 5A-5E show immunoblot analysis demonstrating the ability of BI-based PROTACs to degrade BRAF and inhibit MEK kinase phosphorylation. Pmd-PEG$_3$-BI (FIG. 5A), Pmd-PEG$_5$-BI (FIG. 5B), Pmd-PEG$_6$-BI, Pmd-PEG$_8$-BI (FIG. 5C), Pmd-PEG$_3$-2C-3C-BI (FIG. 5D), V032-PEG$_4$-BI (FIG. 5E) and the parent inhibitor BI882370 (FIGS. 5A-5E) were incubated with A375 human melanoma cells for 24 hrs. Degradation of BRAF$^{V600E}$ was observed for the Pmd-BI series. No degradation of BRAF$^{V600E}$ was observed with VHL-BI.

The invention claimed is:

1. A compound of Formula I or a pharmaceutically acceptable salt and/or solvate thereof:

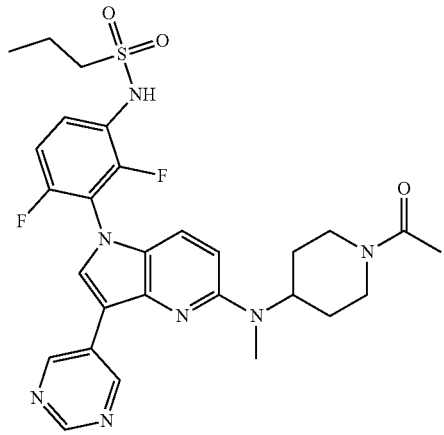

I wherein

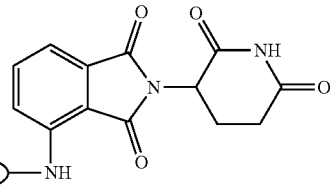

is a linker group, and

represents a point of covalent attachment.

2. The compound of claim 1, wherein

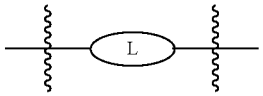

comprises at least one $C_{1-14}$alkylene, optionally interrupted by one or more heteromoieties selected from O, S, and NR and optionally interrupted by one or two amides and/or one triazole, wherein R is $C_{1-4}$alkyl.

3. The compound of claim 1, wherein

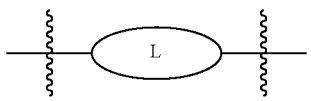

is a group of Formula II:

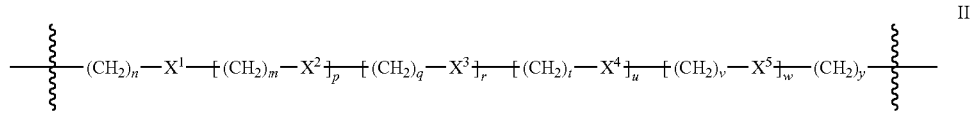

II wherein

represents a point of covalent attachment;
X$^1$ is O, S, NR, C(O)NH or CH$_2$;
X$^2$ is O, S or NR;
X$^3$ is O, S, NR or triazole;
X$^4$ is O, S or NR;
X$^5$ is O, S, NR or C(O)NH;
n and y are integers independently selected from 1 to 6;
m, q, t, and v are integers independently selected from 1 to 3;
p and u are integers independently selected from 0 to 14;
r and w are independently 0 or 1, and
R is $C_{1-4}$alkyl.

4. The compound of claim 3, wherein n and y are integers independently selected from 1 to 4.

5. The compound of claim 3, wherein X$^1$, X$^2$, X$^3$, X$^4$ or X$^5$ and O.

6. The compound of claim 3, wherein r, u and w are O.

7. The compound of claim 3, wherein p is an integer selected from 1-8.

8. The compound of claim 1, wherein

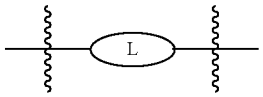

is a group of Formula III:

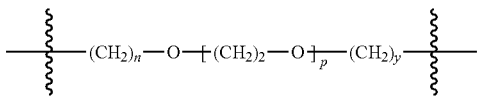

III wherein

represents a point of covalent attachment;
n and y are integers independently selected from 1 to 4; and
p is an integer selected from 0 to 14.

9. The compound of claim 8 wherein n and y are independently 2 or 3 and p is selected from 1-8.

10. The compound of claim 1, wherein

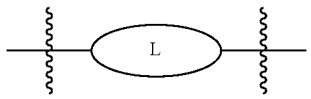

is a group of Formula IV:

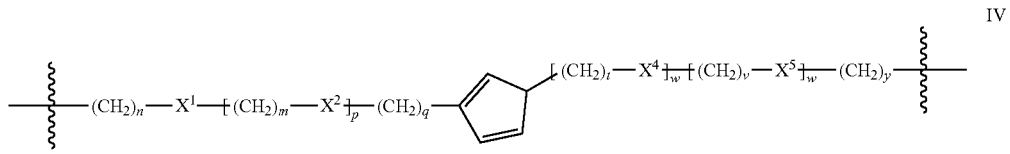

IV wherein

represents a point of covalent attachment;
$X^1$ is O, S, NR, C(O)NH or $CH_2$;
$X^2$ is O, S or NR;
$X^4$ is O, S or NR;
$X^5$ is O, S, NR or C(O)NH;
n and y are integers independently selected from 1 to 6;
m, q, t, and v are integers independently selected from 1 to 3;
p and u are integers independently selected from 0 to 14;
w is 0 or 1, and
R is $C_{1-4}$alkyl.

11. The compound of claim 3, wherein, $X^1$ is C(O)NH.
12. The compound of claim 11, wherein w is O.
13. The compound of claim 1, wherein

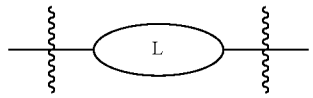

is a group of Formula V:

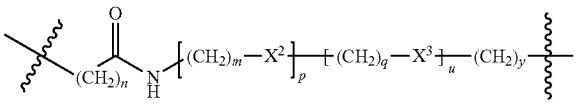

V wherein

represents a point of covalent attachment;
$X^2$ is O, S or NR;
$X^3$ is O, S, NR or triazole;
n and y are integers independently selected from 1 to 6;
m and q are integers independently selected from 1 to 3;
p and u are integers independently selected from 0 to 14, and
R is $C_{1-4}$alkyl.

14. The compound of claim 1, wherein

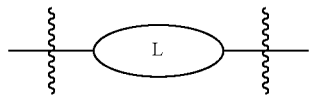

is selected from the groups listed below:
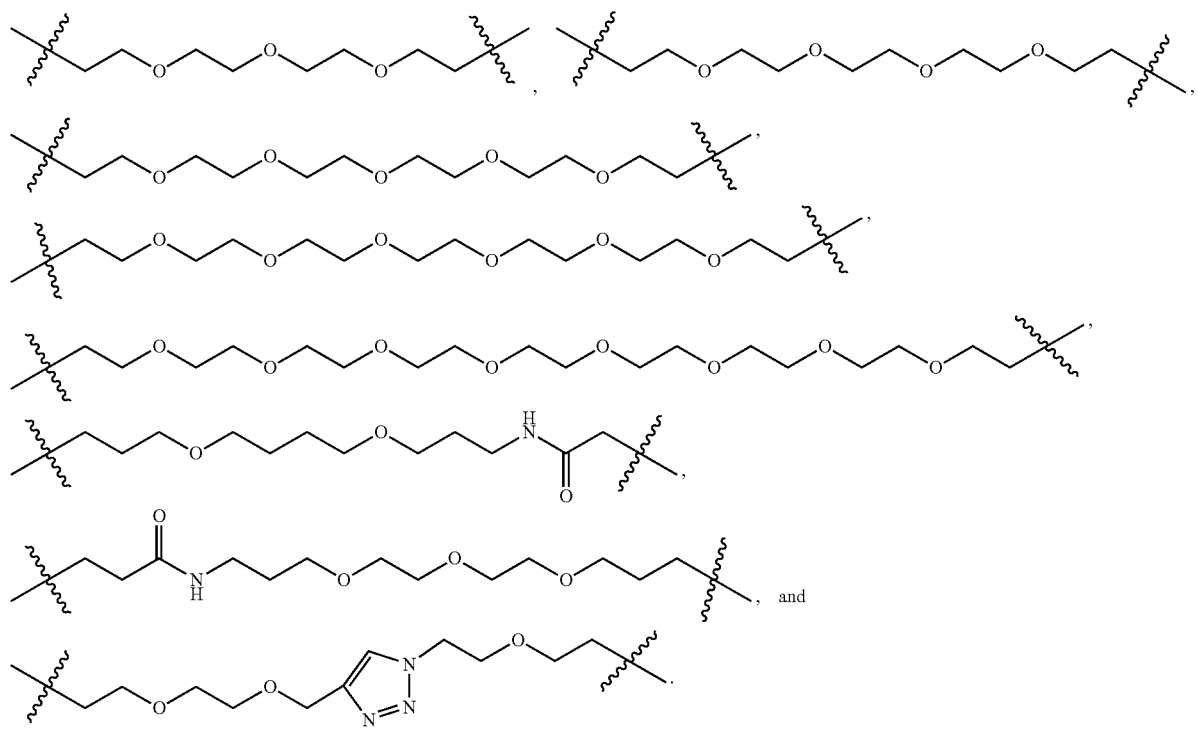
15. The compound of claim 1, wherein the compound of Formula I is selected from the compounds listed below:
| Compound I.D | Example # | Structures |
|---|---|---|
| I-1 | 1 | 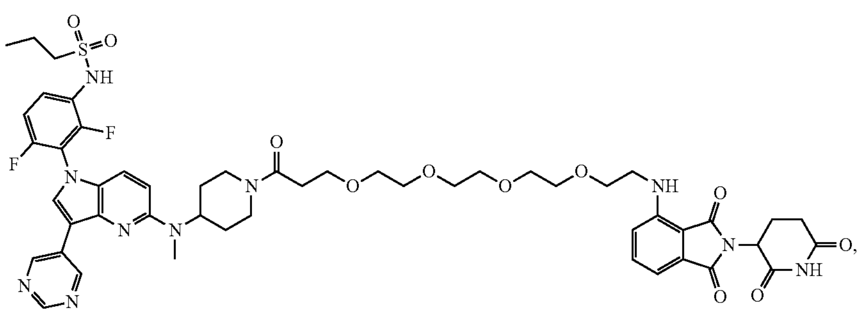 [SMILES: CCCS(=O)(=O)Nc1ccc(F)c(-n2cc(-c3cncnc3)c3nc(N(C)C4CCN(C(=O)CCOCCOCCOCCOCCNc5cccc6c5C(=O)N(C5CCC(=O)NC5=O)C6=O)CC4)ccc32)c1F] |
| I-2 | 2 | 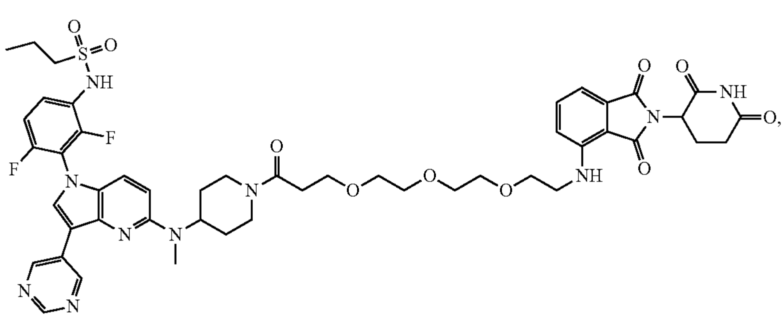 [SMILES: CCCS(=O)(=O)Nc1ccc(F)c(-n2cc(-c3cncnc3)c3nc(N(C)C4CCN(C(=O)CCOCCOCCOCCNc5cccc6c5C(=O)N(C5CCC(=O)NC5=O)C6=O)CC4)ccc32)c1F] |

| Compound I.D | Example # | Structures |
|---|---|---|
| I-3 | 3 | 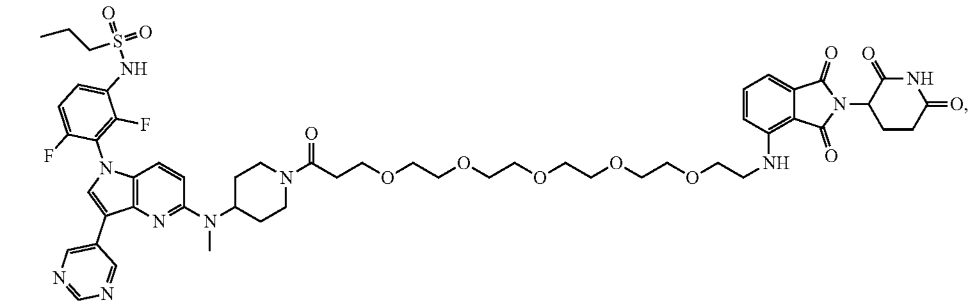 [SMILES: CCCS(=O)(=O)Nc1ccc(F)c(-n2cc(-c3cncnc3)c3nc(N(C)C4CCN(C(=O)CCOCCOCCOCCOCCOCCNc5cccc6c5C(=O)N(C5CCC(=O)NC5=O)C6=O)CC4)ccc32)c1F] |
| I-4 | 4 | 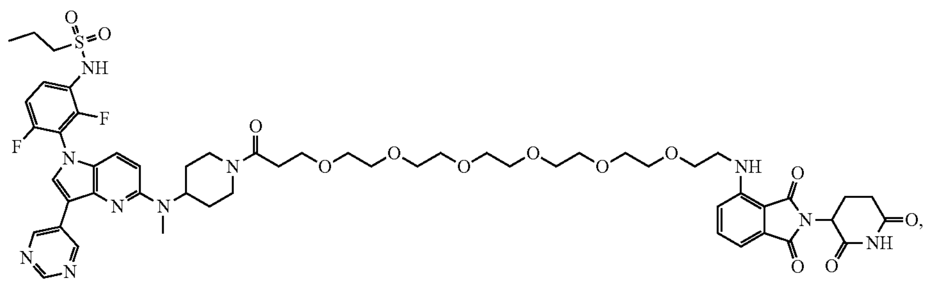 [SMILES: CCCS(=O)(=O)Nc1ccc(F)c(-n2cc(-c3cncnc3)c3nc(N(C)C4CCN(C(=O)CCOCCOCCOCCOCCOCCOCCNc5cccc6c5C(=O)N(C5CCC(=O)NC5=O)C6=O)CC4)ccc32)c1F] |
| I-5 | 5 | 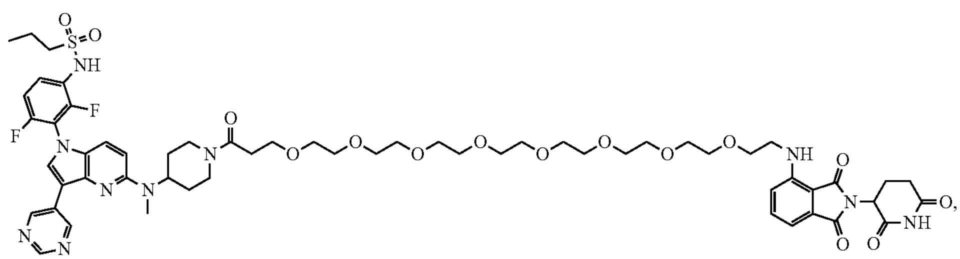 |
| I-6 | 6 | | or a pharmaceutically acceptable salt, and/or solvate thereof.

16. A composition comprising one or more compounds of claim 1 and a carrier.

17. A method of treating a disease, disorder or condition that is mediated or treatable by inhibiting and/or degrading V600E mutant B-Raf protein comprising administering a therapeutically effective amount of one or more compounds of claim 1 to a subject in need thereof, wherein the disease, disorder or condition is cancer.

18. The method of claim 17 wherein the cancer is one that is impacted or mediated by mutations in the RAS-RAF-ERK signaling pathway or the cancer is one that is impacted or mediated by mutations in b-Raf.

19. The method of claim 17, wherein the cancer is selected from melanoma, non small cell lung cancer, glioma, thyroid cancer and colorectal cancer.

20. The method of claim 17, wherein the subject is human.

* * * * *